US006770195B2

(12) United States Patent
Young et al.

(10) Patent No.: US 6,770,195 B2
(45) Date of Patent: Aug. 3, 2004

(54) COMPACT AUTOMATED RADIONUCLIDE SEPARATOR

(75) Inventors: John E. Young, Woodridge, IL (US); John J. Hines, Newark, IL (US)

(73) Assignee: PG Research Foundation, Inc., Darien, IL (US)

( * ) Notice: Subject to any disclaimer, the term of this patent is extended or adjusted under 35 U.S.C. 154(b) by 109 days.

(21) Appl. No.: 10/178,003

(22) Filed: Jun. 21, 2002

(65) Prior Publication Data

US 2002/0195391 A1 Dec. 26, 2002

Related U.S. Application Data

(60) Provisional application No. 60/300,134, filed on Jun. 22, 2001.

(51) Int. Cl.[7] .............................................. B01D 15/08
(52) U.S. Cl. .................... 210/198.2; 210/143; 210/656; 422/70; 422/903; 423/2
(58) Field of Search ................................. 210/656, 143, 210/198.2; 423/2, 249; 422/70, 903

(56) References Cited

U.S. PATENT DOCUMENTS

| | | | | |
|---|---|---|---|---|
| 4,600,566 | A | * | 7/1986 | Fujine et al. ............. 423/179.5 |
| 5,110,474 | A | * | 5/1992 | Horwitz et al. ................ 588/20 |
| 5,695,720 | A | | 12/1997 | Wade et al. .................... 422/82 |
| 5,729,821 | A | * | 3/1998 | Knapp et al. ................... 423/2 |
| 5,774,782 | A | * | 6/1998 | Mirzadeh et al. .............. 423/2 |
| 5,854,968 | A | | 12/1998 | Horwitz et al. ................. 423/2 |
| 6,126,909 | A | | 10/2000 | Rotmensch et al. ........... 423/2 |
| 6,153,154 | A | | 11/2000 | Egorov et al. .................. 423/2 |
| 6,157,036 | A | * | 12/2000 | Whiting et al. ........ 250/432 PD |
| 6,245,305 | B1 | * | 6/2001 | Bray et al. ....................... 423/2 |
| 6,485,695 | B1 | * | 11/2002 | Koch et al. ...................... 423/2 |
| 6,603,127 | B1 | * | 8/2003 | Scheinberg et al. ... 250/432 PD |

OTHER PUBLICATIONS

Whitlock, Inc. Eng. Chem. Res. (2000), 39:3135–3139.
Hassfjell et al., Chem Rev. (2001) 101: 2019–2036.
Imam, J. Radiation Oncology Biol. Phys. (2001) 51:271–278.
McDevitt et al., Science (2001) 294:1537–1540.
Choppin et al., T. Nuclear Chemistry: Theory and Applications; Pergamon Press: Oxford, 1980.
Gansow et al., In Radionuclide Generators: New Systems for Nuclear Medicine Applications.
Knapp et al. Eds., Radionuclide Generators: New Systems for Nuclear Medicine Applications, American Medical Society: Washington, DC (1984) vol. 241.
Dietz et al., Appl. Radiat, Isot. (1992) 43:1093–1101.
Mirzadeh et al., J. Radioanal Nucl. Chem. (1996) 203:471–488.
Lambrecht et al, Radiochim. Acta (1997) 79:141–144.
Wu et al., Radiochim Acta (1997) 79:141–144.

* cited by examiner

*Primary Examiner*—Ernest G. Therkorn
(74) *Attorney, Agent, or Firm*—Welsh & Katz, Ltd.

(57) ABSTRACT

A method and apparatus are provided for automatically separating radionuclides using a chromatographic separation process. The method includes the steps of displaying a first flow diagram on a display depicting flow of the radionuclides through a first set of separation elements of the plurality of separation processing elements, but only during a first step of the chromatographic separation process and displaying a second flow diagram on the display depicting flow of the radionuclides through a second set of separation elements of the plurality of separation processing elements, but only during a second step of the chromatographic separation process.

23 Claims, 17 Drawing Sheets

COMPACT AUTOMATED RADIONUCLIDE SEPARATOR

REFERENCE TO RELATED APPLICATIONS

This application claims the benefit of U.S. Provisional Application No. 60/300,134, filed Jun. 22, 2001.

The field of the invention relates to nuclear medicine. More particularly, the invention relates to methods of producing radioactive materials of high radionuclidic and chemical purity for use in nuclear medicine.

The use of radioactive materials for nuclear medicine is known. Radioactive materials may be used for any of a number of diagnostic and therapeutic purposes. For example, in the case of diagnostic medicine, radioactive materials (i.e., a tracer) may be injected into an arm vein of a patient, and the distribution of the radioactive substance within the body or a part of the body may be portrayed in a series of images. The images may be based upon the emission of gamma rays by the tracer. As the radioactive materials within the tracer decay, the gamma rays may pass out of the body and be recorded by a scintillation camera. The scintillation camera contains a radiation detector that detects the interaction of gamma rays with the detector and where on a face of the detector the interaction has occurred. The interactions may be used to produce a picture or image of where the gamma rays originated from within the body.

Alternatively, radioactive materials of relatively short half-life (e.g., 2–72 hours) may be used for therapeutic purposes, for example, in the treatment of certain types of tumors (e.g., cancerous tumors). Typically, such materials are coupled to a biolocalization agent that concentrates at the site of the tumor. By localizing the materials at the site of the tumor, the radiation may have a maximum effect on the tumor before natural decay reduces the radiation level or blood circulation carries the material away to other parts of the body.

Often the radioactive material used for diagnostic or therapeutic purposes is tailored for the application. Where the site has a relatively high circulation rate, a material with a very short half-life may be used. Where the circulation rate is lower a material with a longer half-life may be used.

While the radioactive materials used in nuclear medicine are very effective, the preparation and handling of such materials has its own difficulties and risks. Because of the short half-lives associated with some materials, they cannot be stored for long periods. Often a material that would have the greatest benefit cannot be used because it cannot be produced in a location convenient for use. Because of the importance of nuclear medicine, a need exists for improved means of providing short half-life radioactive materials of high radionuclidic and chemical purity.

SUMMARY

A method and apparatus are provided for automatically separating radionuclides using an chromatographic separation process. The method includes the steps of displaying a first flow diagram on a display depicting flow of the radionuclides through a first set of separation elements of the plurality of separation processing elements, but only during a first step of the chromatographic separation process and displaying a second flow diagram on the display depicting flow of the radionuclides through a second set of separation elements of the plurality of separation processing elements, but only during a second step of the chromatographic separation process.

BRIEF DESCRIPTION OF THE DRAWINGS

FIGS. 7–17 depict steps of a separation process that may be provided by the system of FIG. 1.

Figure 1:
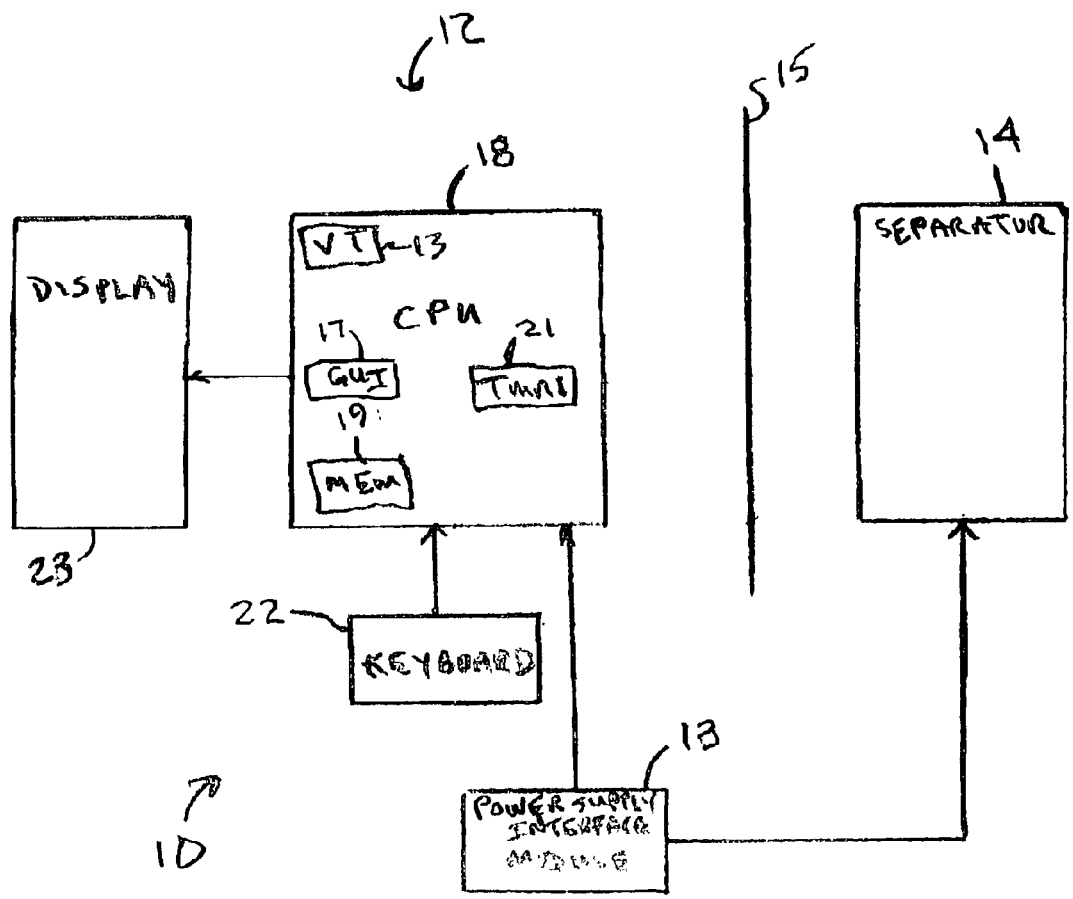
FIG. 1 is a block diagram of an apparatus for separating radionuclides in accordance with an illustrated embodiment of the invention.

Appendix I is a source code listing of source code that may be used by the system of FIG. 1.

DETAILED DESCRIPTION OF A PREFERRED EMBODIMENT

FIG. 1 is a block diagram of a separation system 10, for the separation of radioactive materials, shown generally. The system 10 provides for the rapid chromatographic separation of clinically useful quantities of highly pure radioactive materials for use in diagnostic or therapeutic nuclear medicine.

The separation system 10 may be used to separate a parent radionuclide from a daughter radionuclide where the daughter radionuclide may be produced by decay of the parent. Separation may occur by trapping the parent radionuclide (i.e., using a conventional generator and the forward COW process) or by trapping the daughter radionuclide (i.e., using a selectivity inversion generator and the reverse COW process). While the system 10 will be described in terms of a multicolumn selectivity inversion generator, it is to be understood that either method may be used.

The system may be fabricated in the form of a lightweight, portable, modular system 10 that is simple to use in radionuclide production facilities, nuclear pharmacies or a medical environment. The modular system 10 may include a computer controller (e.g., a laptop computer) 12, a power supply/interface module 13, radioactivity shield 15 and a separation module 14. The shield 15 may be of any appropriate material (e.g., glass, plexiglass, plastic, lead, depleted uranium) and may be positioned between the laptop 12 and the separation unit 14 for the protection of the operator (not shown) during the separation process.

Lightweight shielding (e.g., plastic, plexiglass, etc.) may be used for separating radionuclides producing low-energy particles (e.g., alpha rays, beta rays, etc.). The heavier shielding materials may be used for high energy gamma rays.

The controller 12 may include a central processing unit (CPU) 18, a keyboard 22 and display 23. An internal memory 19 may be provided for the storage and retrieval of separation programs and set points. One or more software timers 21 may be provided for controlling the separation process.

While the controller 12 will be described in terms of control using the keyboard 22, it should be understood that the keyboard 22 may be replaced by touchscreen technology or other advanced user input device. Accordingly, the controller 12 may include appropriate hardware and software to support a touchscreen interface.

Figure 2:
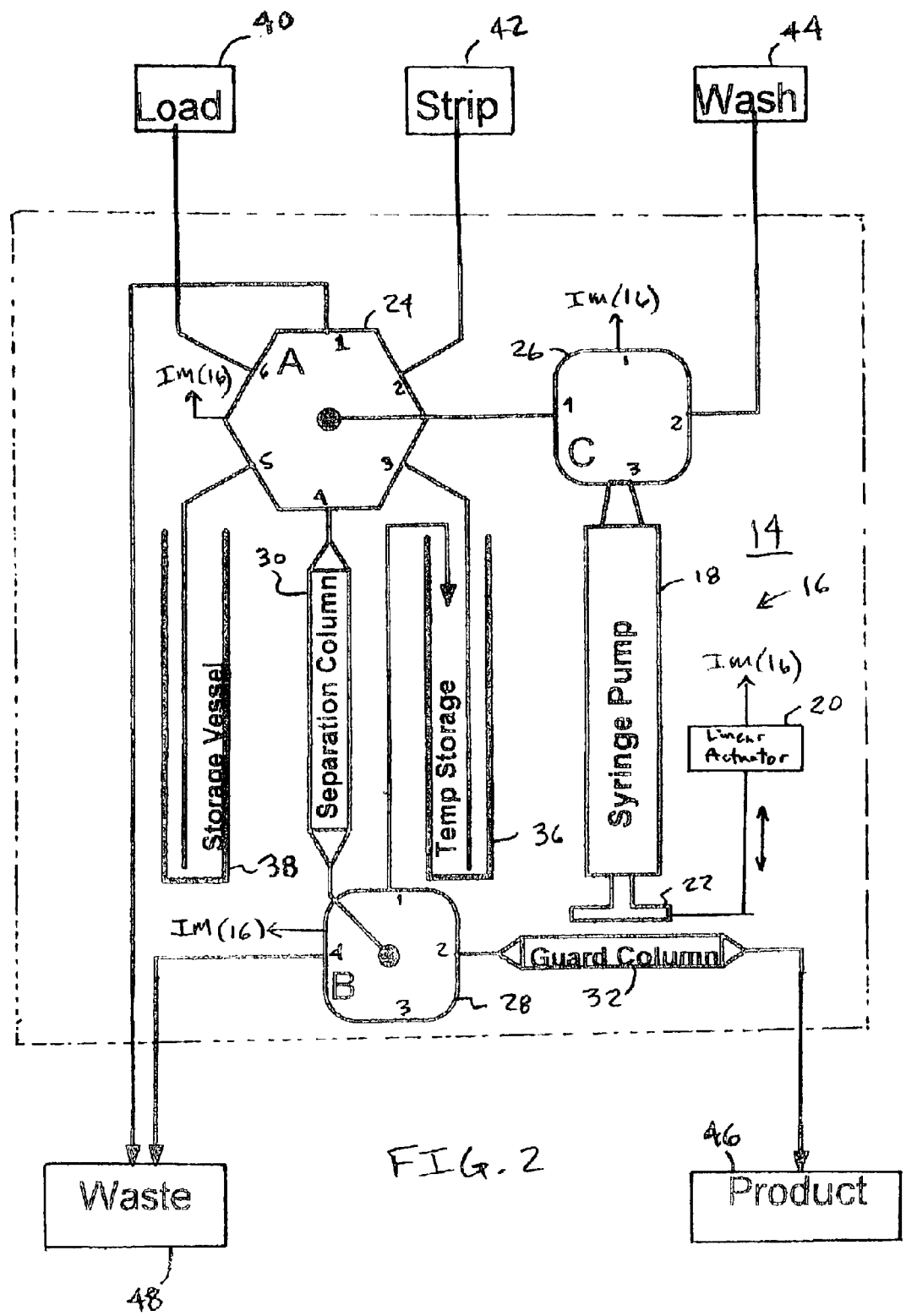
FIG. 2 is a connection diagram of a separation module that may be used with the system of FIG. 1.

FIG. 2 is a connection diagram of the processing elements of the separation module 14 of FIG. 1 in more detail. The separation module 14 may include a high speed syringe pump 16, multiport valves 24, 26, 28 and a set of chromatographic columns 30, 32 containing one or more materials with high chemical selectivities.

The separation module 14 may be remotely controlled by the computer system 12 through interface 13. The control of the separation module 14 by the computer 12 simplifies operation and enforces strict adherence to approved protocols for radionuclide purification. The small size of the separation module 14 simplifies shielding and, when combined with remote operation, the module 14 minimizes radiation exposure to the clinical staff and/or patient.

The separations chemistry, hardware and software can be readily adapted to meet any of a range of needs of the nuclear medical practitioner. For example, the system 10 is particularly well suited for use as a radionuclide generator in that separations can be performed rapidly (e.g., in less than 5 minutes) to yield an ultrahigh purity product (e.g., decontamination factors of $10^6$ or greater). The ultra-high purity of the end product is enhanced by a unique guard column 32 that follows the primary separation column 30.

Separation columns 30, 32 can be selected for purification of a wide range of radionuclides, depending upon the diagnostic or therapeutic objectives. The apparatus has been found to be particularly well suited for the purification of yttrium-90, bismuth-212 and 213, or rhenium-188 for radiotherapy or technetium-99 m, thallium-201, fluorine-18 or indium-111 for diagnostic imaging.

Turning now to the specifics of the system 10, an explanation will be provided of the hardware and software. Following an explanation of the hardware and software, an example will be provided of the use of the system 10.

The transport of radionuclides within the system 10 relies upon the syringe pump 16 and multiport valves 24, 26, 28. The syringe pump 16 may be any small volume device with a relatively precise volume control (e.g., a model MBP2000 syringe pump provided by Advanced Liquid Handling of Milwaukee, Wis.). The syringe pump 16 may include a syringe body 18 and linear actuator 20. The syringe body 18 may be a variable displacement device (e.g., with a maximum capacity of 5 milliliters (ml), 10 ml, etc.).

The linear actuator 20 may provide a resolution of 2000 steps between a maximum volume state of the syringe body 18 and a zero volume state of the syringe body 18. For example, under one embodiment the syringe body 18 may have a maximum volume state of 5 ml. However, any size syringe 18 may be used.

The step rate at which the controller 12 drives the linear actuator 20 defines the flow rate into or out of the syringe body 18. For example, if the syringe body 18 has a maximum volume of 5 ml and the linear actuator has 2000 positions between maximum and zero volume, then each step of (i.e., actuating pulse applied to) the actuator 20 results in a volume change within the syringe body 18 of 0.0025 ml. At a rate of one pulse per second, the flow rate into or out of the syringe pump 16 would be 0.0025 ml/second. Alternatively, the linear actuator 20 may be driven at a rate of up to 2000 pulses/s resulting in a flow rate of 5 ml/s, or any rate in between.

The multiport valves may be sized to accommodate expected flow rates from the syringe pump 16. Multiport valve A 24 may be any appropriately sized multi-position valve (e.g., a Model 6-5 MVP plug valve, 6 port distribution, by Hamilton Co., Reno, Nev.) with a common port connected to multiport valve C 26. Similarly, multiport valve B 28 may be an appropriately sized multi-position valve (e.g., a Model 4-5 MVP, plug valve, 4-port distribution by Hamilton Co.) with common port connected to the separation column 30. Multiport valve C 26 may be a 4-port special valve supplied as a part of the assembly of the syringe pump 16 (as provided for in the part number given above for the syringe pump 16) or may be supplied as a separate, stand-alone valve assembly. Appropriate valve positioners (e.g., a Hamilton 'Modular Valve Positioner' (MVP) with digital TTL communications) may be used as elements of the interface module 13. Additional valve positioners and syringe pumps may be connected to the interface module 13 to provide additional fluid delivery and control capabilities.

The separation column 30 and guard column 32 may be fabricated as cylindrical structures (e.g., ½ inch×2 inches) with tubing connections on each end. The separation column 30 and guard column 32 may be filled with a chromatographic material (e.g., ion-exchange resin, extraction chromatographic material, etc.) appropriate for the radionuclide to be separated. The guard column 32 may include one, two or more discrete segments (three shown in the figures) of separation materials.

The separation elements 16, 24, 26, 28, 30, 32, 36, 38 and external containers 40, 42, 44, 46, 48 may be connected using an appropriate chemical resistant tubing (e.g., Teflon). The tubing and fittings may be provided with a diameter (e.g., 2 mm) intended to reduce the deadspace within the separation module 14.

The controller 12 may be provided with a graphical user interface (GUI) 17 that provides instantaneous flow diagrams and process parameters on the display 23. The flow diagrams and process parameters allow an operator to monitor operation of the module 14 without directly viewing the module 14. Monitoring the mechanical operations of the module 14 is important since the operator may not be able to directly view the module 14 during operation because of the radiation that may be emitted by the materials processed within the separation module 14.

The sequence of valve and pump operations of the separator 14 may be controlled by a customized protocol stored in the memory 19 of the controller 12. The operator may use predefined existing protocols or may create a new protocol. To create a new protocol, the operator may click on a specific icon on the display and proceed to manually enter operational parameters directly. Alternatively, a specialized graphical user interface may be provided to allow the operator to create new protocols. As a further alternative, the operator may be prompted to enter identifiers of devices and operational activities.

Figure 3:
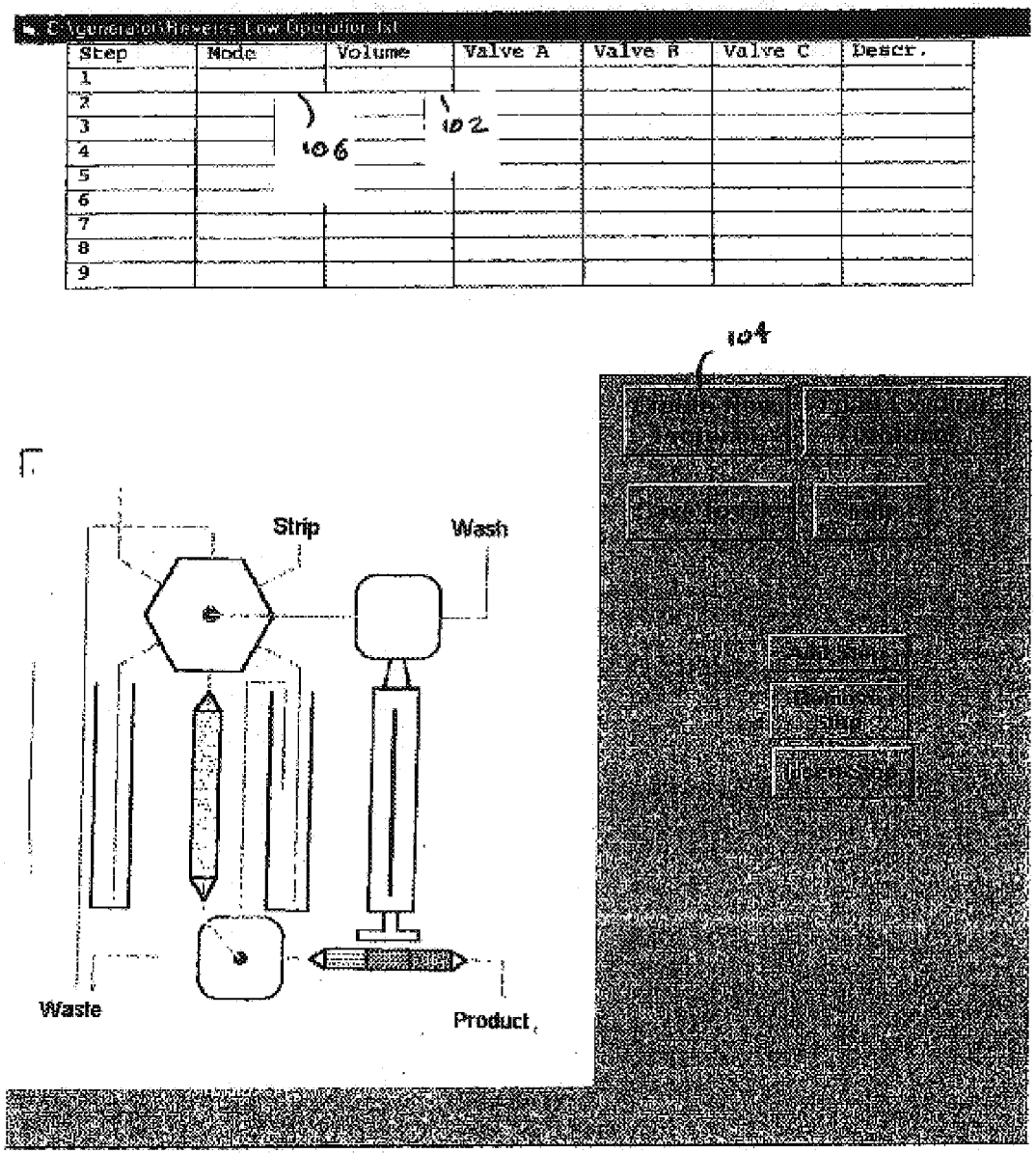
FIG. 3 is a programming screen that may be used with the system of FIG. 1.

Upon startup of the protocol creation software, a programming screen 100 (FIG. 3) may be presented to the operator. To create a new separation program, the operator may click on a "Create New Protocol" button 104.

Figure 4:
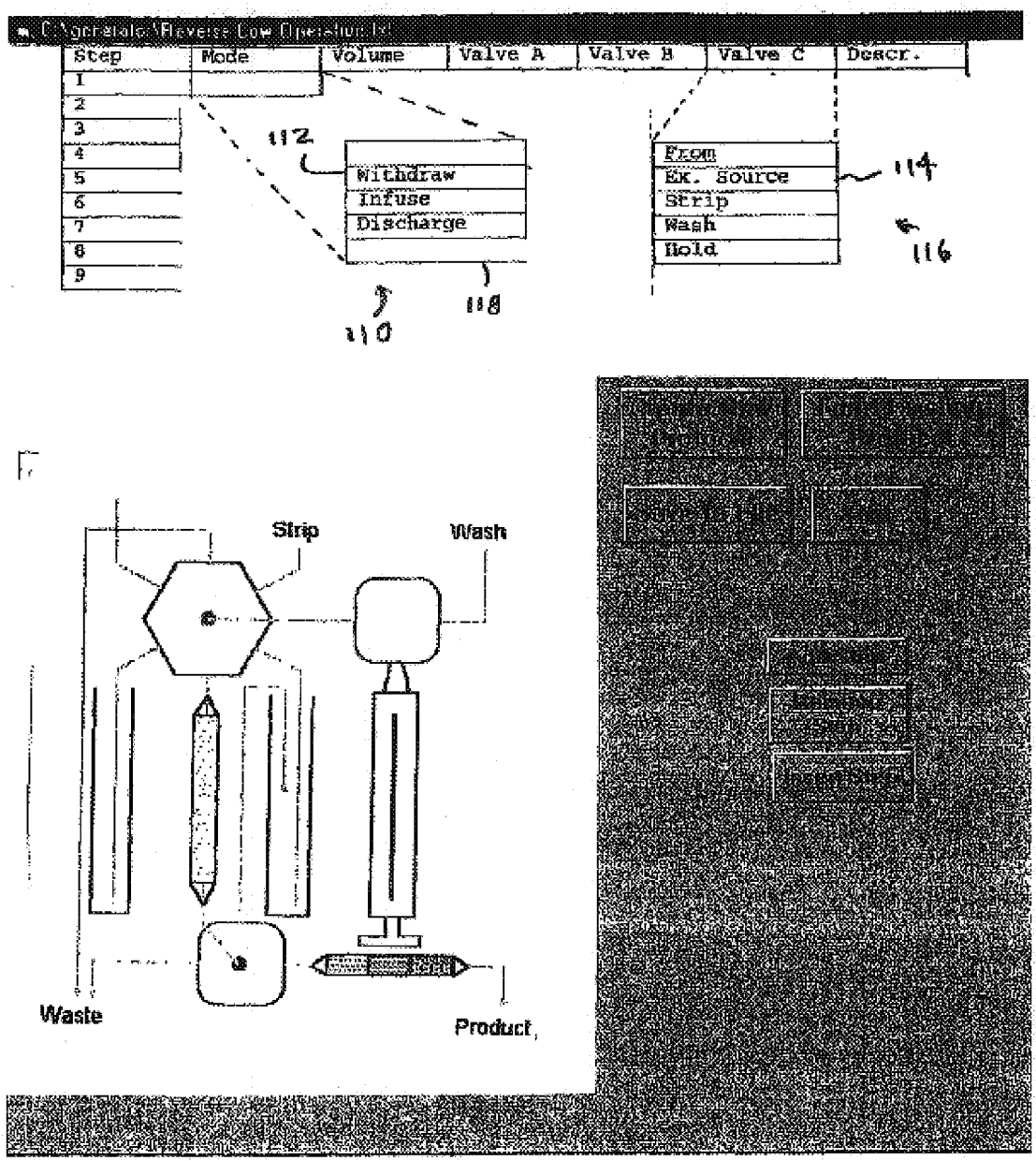
FIG. 4 depicts programming steps that may be used with the system of FIG. 1.

Next, the operator may click on a mode box 106. In response, the controller 12 may present the operator with a selection box 110 (FIG. 4) offering the operator a number of possible operations. The operator may click on the Withdraw box 112. The operator may then click on Valve A, Valve B or Valve C boxes to define values for the positions of the valves 24, 28, 26, respectively, to execute the selected step. Defining values may simply mean entry of a port number shown in FIG. 2 in the box appearing directly below the valve identifier.

For example, if after clicking on the Withdraw box 112 the operator should click on the Valve C box, then the box 116 may appear offering the operator a number of sources to withdraw material from. Clicking on 'Strip' may automatically program Valves A and C. Alternatively, the operator may click on and program the valves individually.

Following selection of a mode, the operator may click on a Volume box 102. Following selection of the Volume box 102, the operator may enter a total volume using the keyboard 22. Using the procedure described herein, the operator may create a separation program appropriate to the radionuclide being processed.

Figure 5:
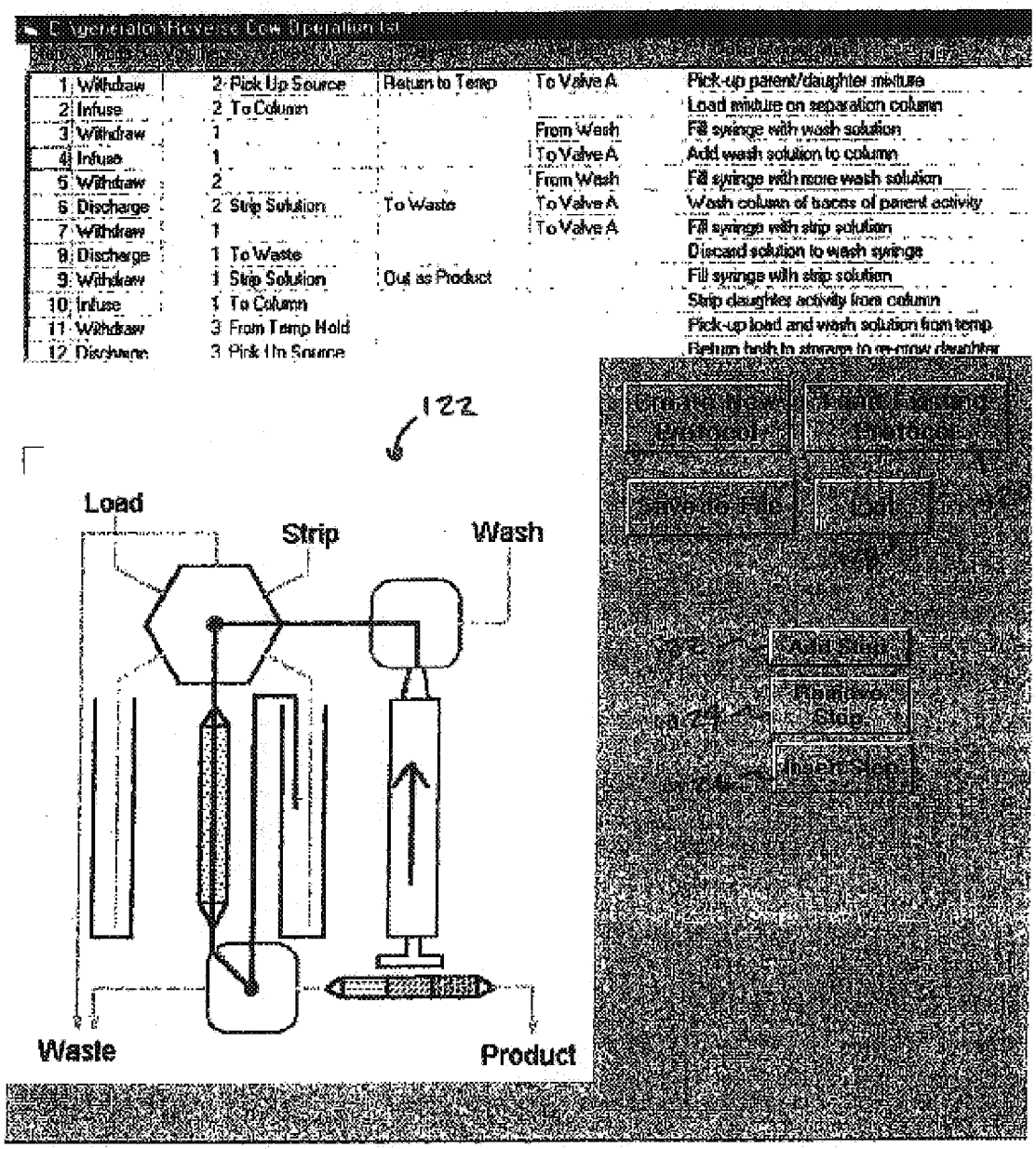
FIG. 5 depicts additional programming steps that may be used with the system of FIG. 1.

As an alternative to creating a new program, the operator may activate a "Load Existing Protocol" box 120 (FIG. 5). The operator may also click on a particular step (e.g., step 4). In response to selecting a particular step, a flow diagram 122 may be presented to the operator displaying the flow provided by the selected step.

The operator may also edit existing programs. For example, the operator may click on an "Add Step" button 122 to add another process step or a "Remove Step" button 124 to remove a step. Alternatively, the operator may click on an "Insert Step" button 126 to insert another step. Upon completing a protocol, the operator may activate a "Save to File" button to save the protocol and then click on Exit to close the protocol preparation program.

Figure 6:
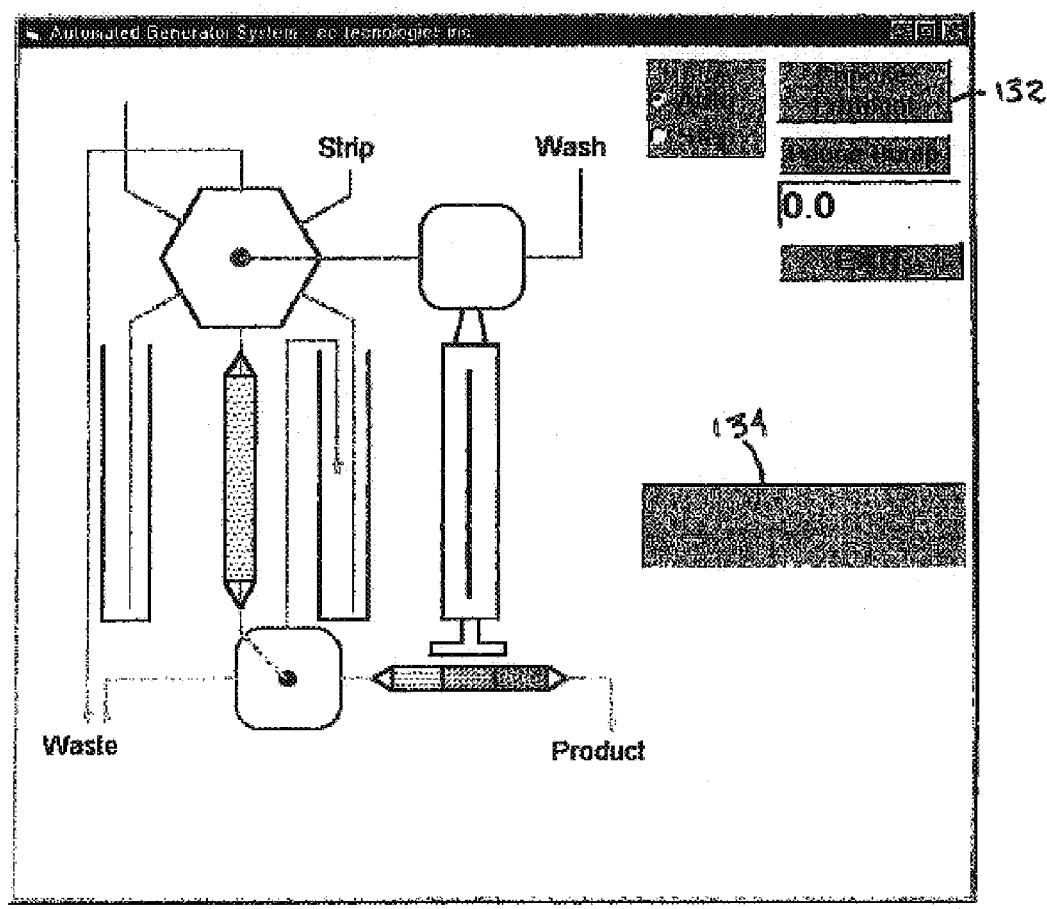
FIG. 6 depicts operation selection steps that may be used with the system of FIG. 1.

To execute a specific protocol, the operator may click on a predefined icon located on the display 23. In response, the controller 12 may present the operator with a protocol selection screen 130 (FIG. 6). The operator may click on a "Choose Protocol" button 132 and enter a protocol identifier in a selection window 134.

FIGS. 7–17 depict program screens that may be used in a particular separation process. For purposes of explanation, it may be assumed that a parent radionuclide has previously been transferred from an external source (shipping container) 40 to an internal storage vessel 38 (FIG. 2).

It also may be assumed that sufficient time has passed for some of the parent radionuclide to have decayed into daughter radionuclide. As such, the storage vessel 38 may contain a mixture of parent and daughter radionuclides.

The program of FIGS. 7–17 may be executed automatically or one step at a time. The execution mode may be selected by a selection switch 148.

When in manual mode, the operator may initiate each step by activating the "START" button 146. During each step of the automatic or manual process, an instantaneous flow diagram (FIGS. 7–17) is presented to the operator showing the process step being executed. A cumulative flow indicator 142 and elapsed time indicator 150 or progress bar may be provided for purposes of monitoring a flow rate.

Figure 7:
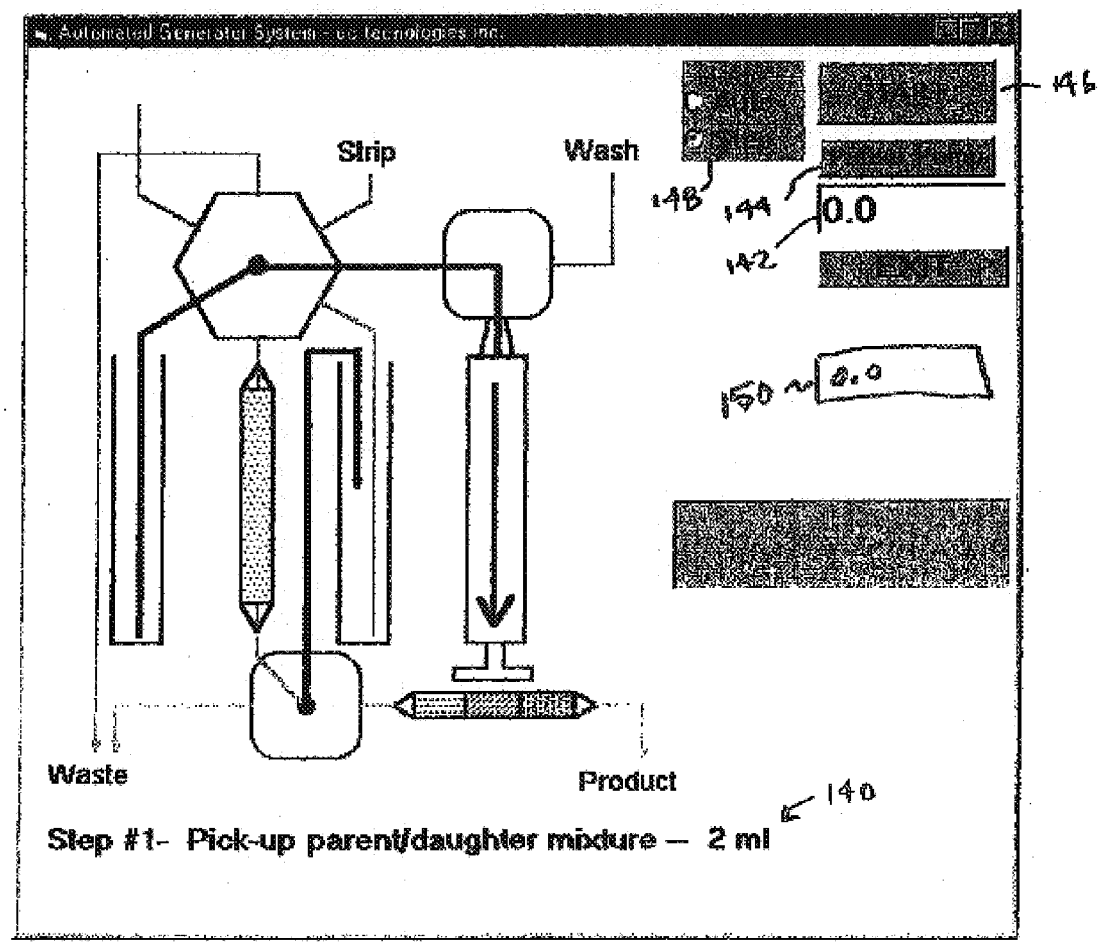

Step #1 of the process is shown in FIG. 7. As shown, the controller 12 has moved Valve A 24 to port #5 (FIG. 1) and Valve C 26 to port #1. The fact that the process has not yet started is reflected in the time display 142 which remains at zero.

As may be seen the selected volume of Step #1 is 2 ml. Once the START button 146 is activated, the controller 12 may initiate the linear actuator 20 to draw the parent radionuclide from the storage container 38.

Figure 8:
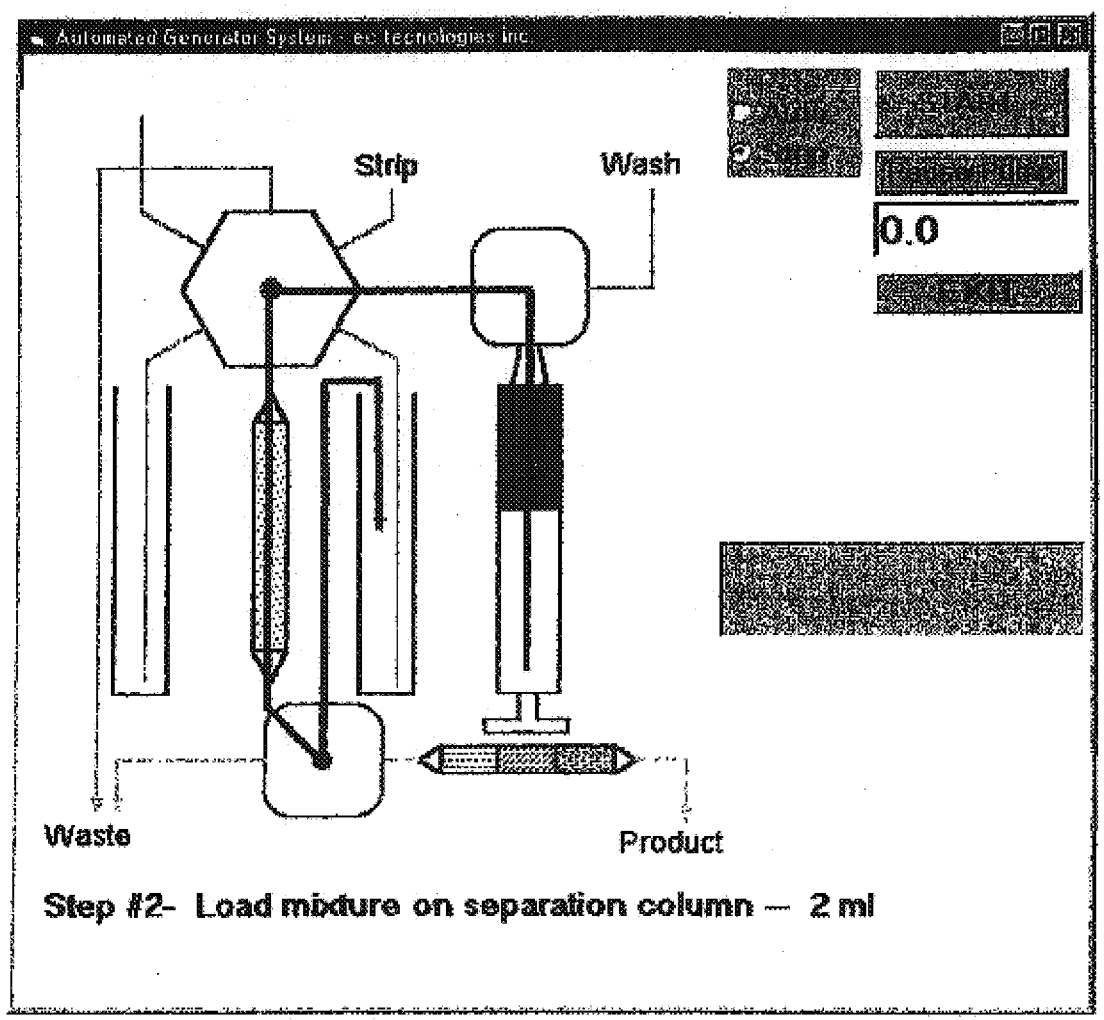

Once the first step is complete, the controller 12 may automatically proceed to the second step (FIG. 8). As shown in FIG. 8, the second step is loading the separation column 30 with the parent and daughter radionuclide.

For Step #2, the controller 12 has moved Valve A 24 to port #4. The position of Valve C 26 has not changed. Valve B 28 has been moved to port #1 to discharge into the temporary storage container 36.

Once the START button 146 is activated, the controller 12 instructs the linear actuator 20 to move a plunger of the syringe body 18 upwards to discharge the parent and daughter radionuclides into the separation column 30.

Within the separation column 30, the daughter radionuclide may be captured within the resin operating as part of a multicolumn selectivity inversion generator. In order to maximize the efficiency of the process, the rate of movement of the plunger may be programmed to accommodate the optimal chromatographic flow rate for use with the separation column 30. In general, a flow rate of 1 ml per second for each square cm of column cross-sectional area (1 ml/min/cm$^2$) may be chosen.

Figure 9:
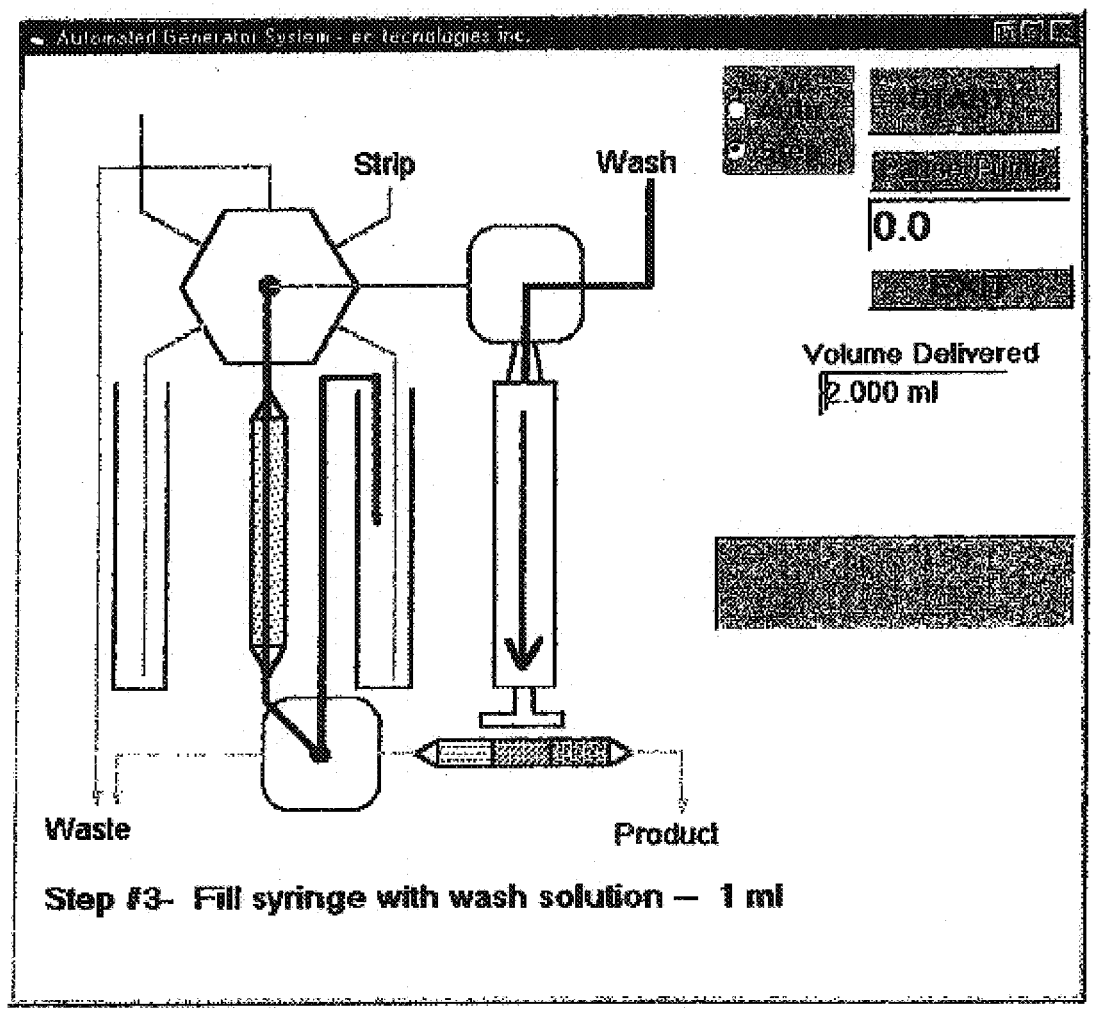
Figure 10:
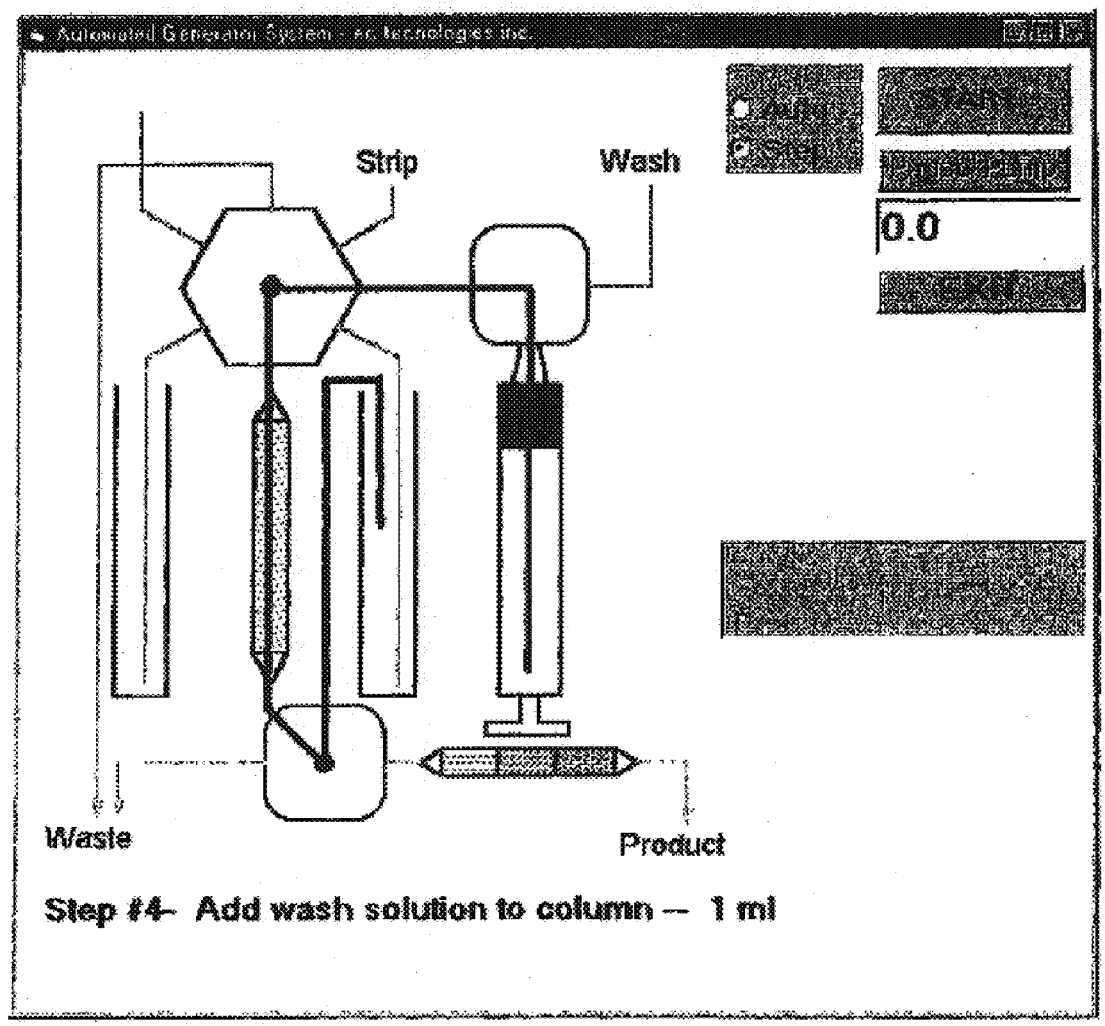
Figure 11:
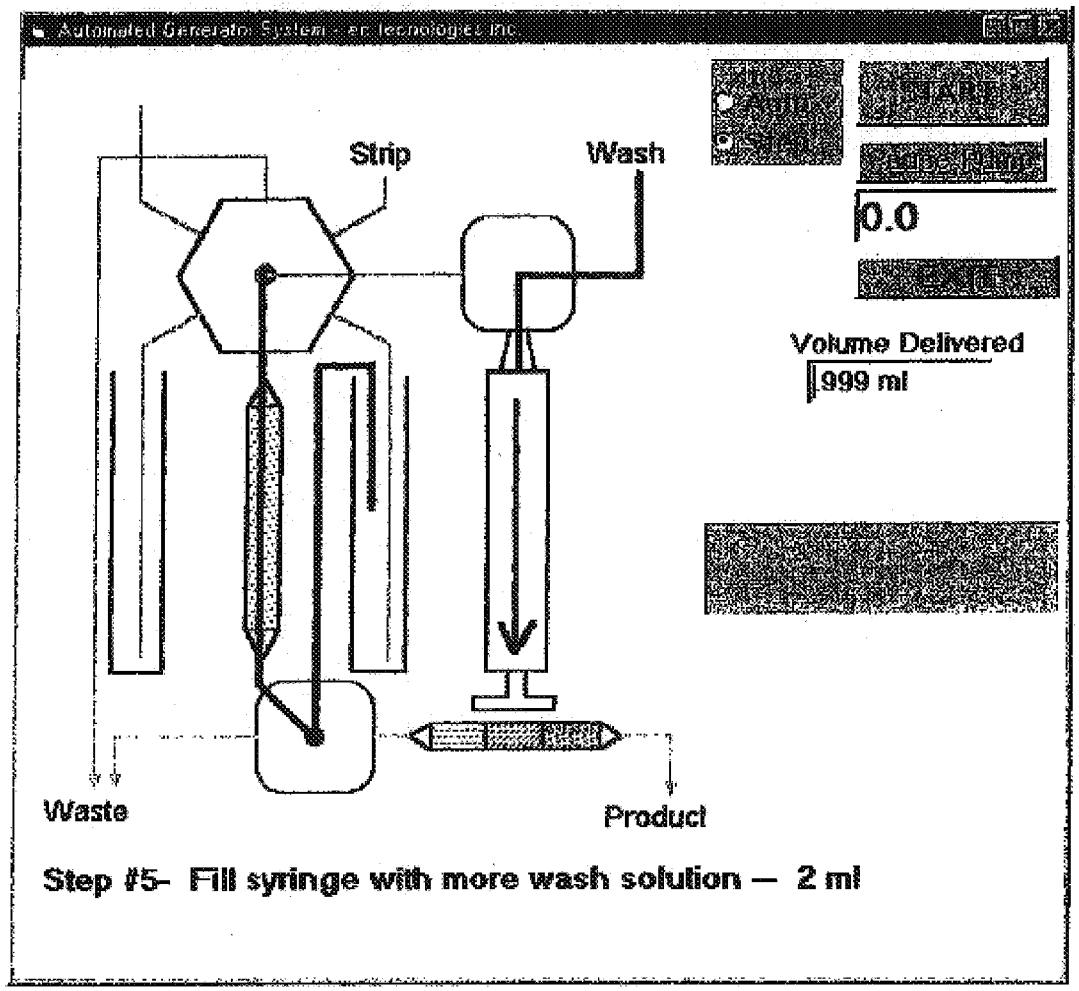
Figure 12:
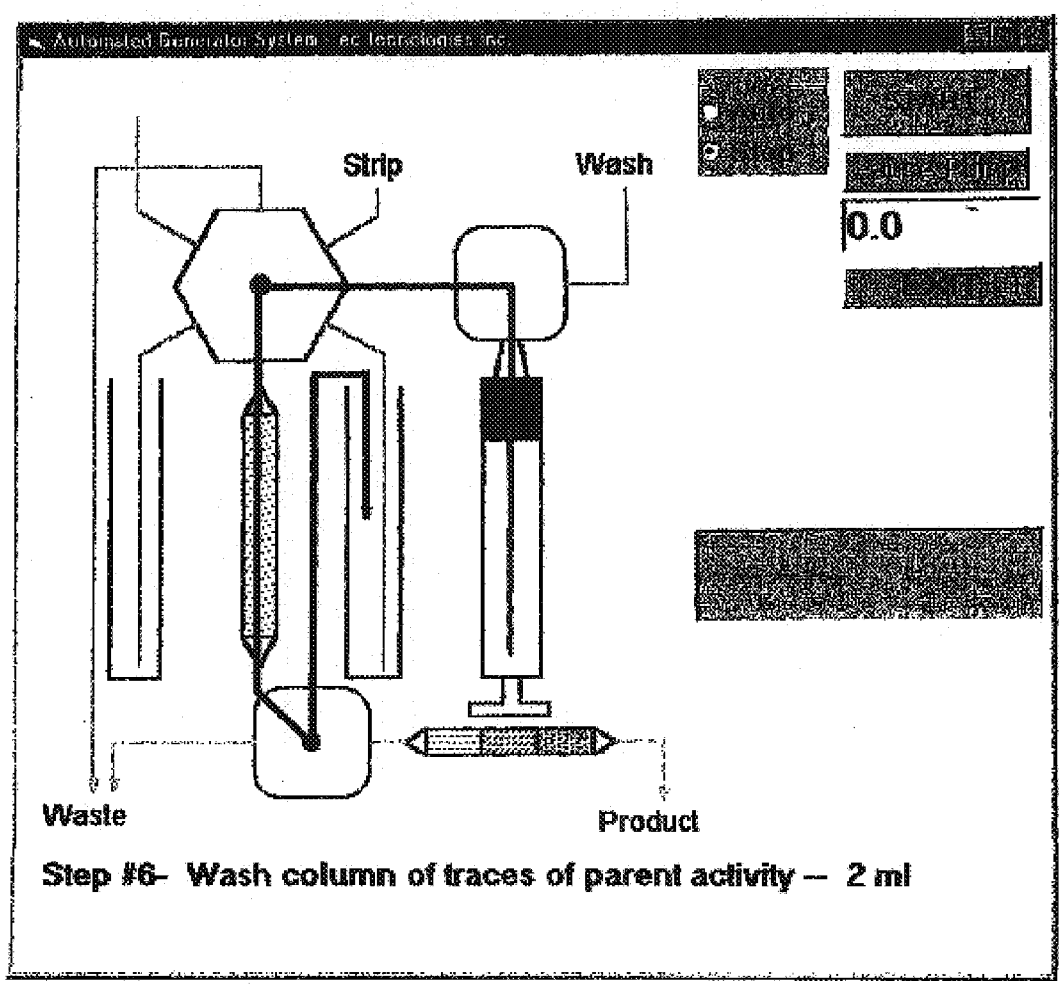

Once the second step is complete, the controller 12 moves to the third step (FIG. 9). In this case, the controller 12 has moved Valve C 26 to port #2 to retrieve a wash solution. In this case, the display shows that 2.000 ml has been delivered through the column 30 and 1 ml is to be loaded as a wash.

In the fourth step (FIG. 10), Valve C 26 has been moved back to port #1. In this case, the wash solution is passed though the separation column 30 to wash any remaining parent radionuclides from the column. In the fifth and sixth steps (FIGS. 11 and 12), the process is repeated.

Figure 13:
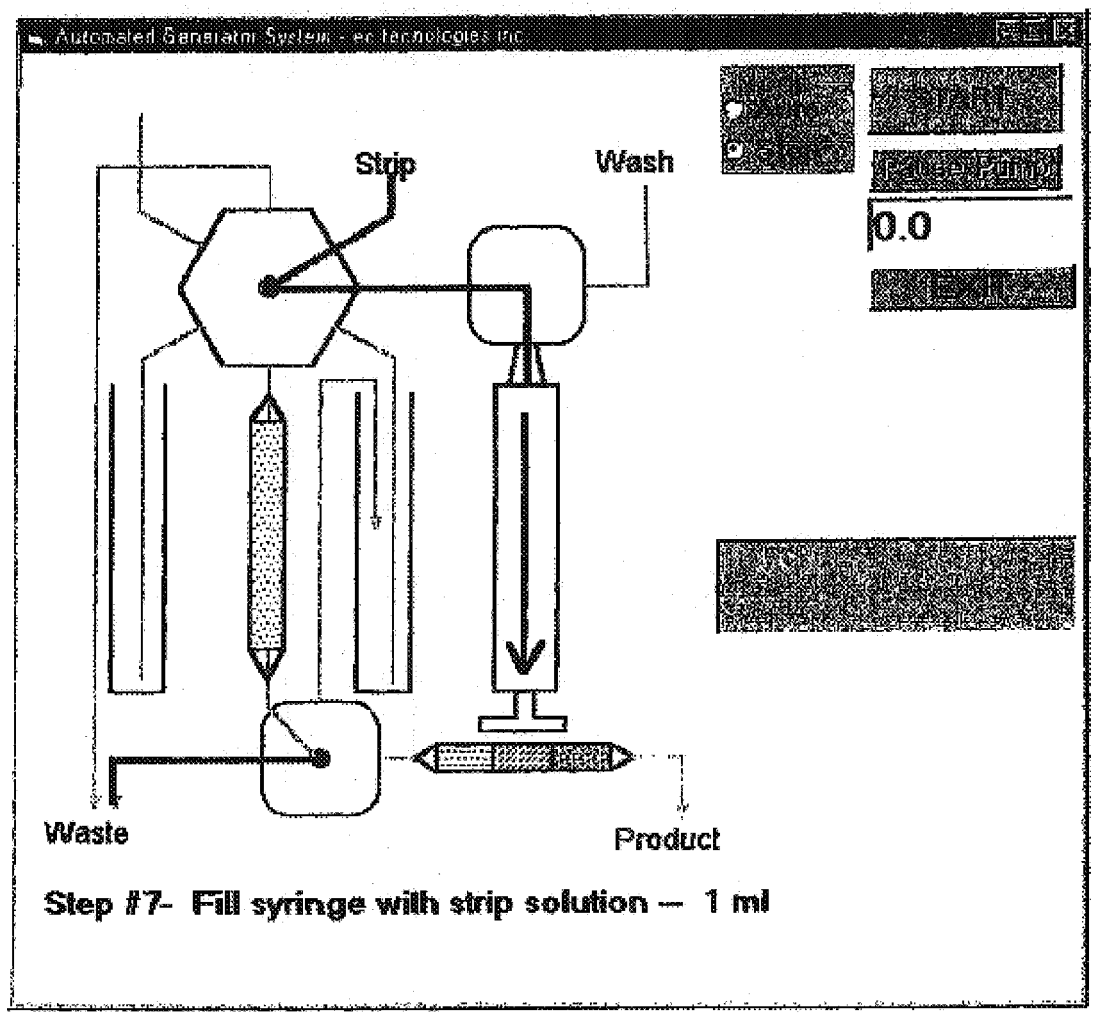
Figure 19:
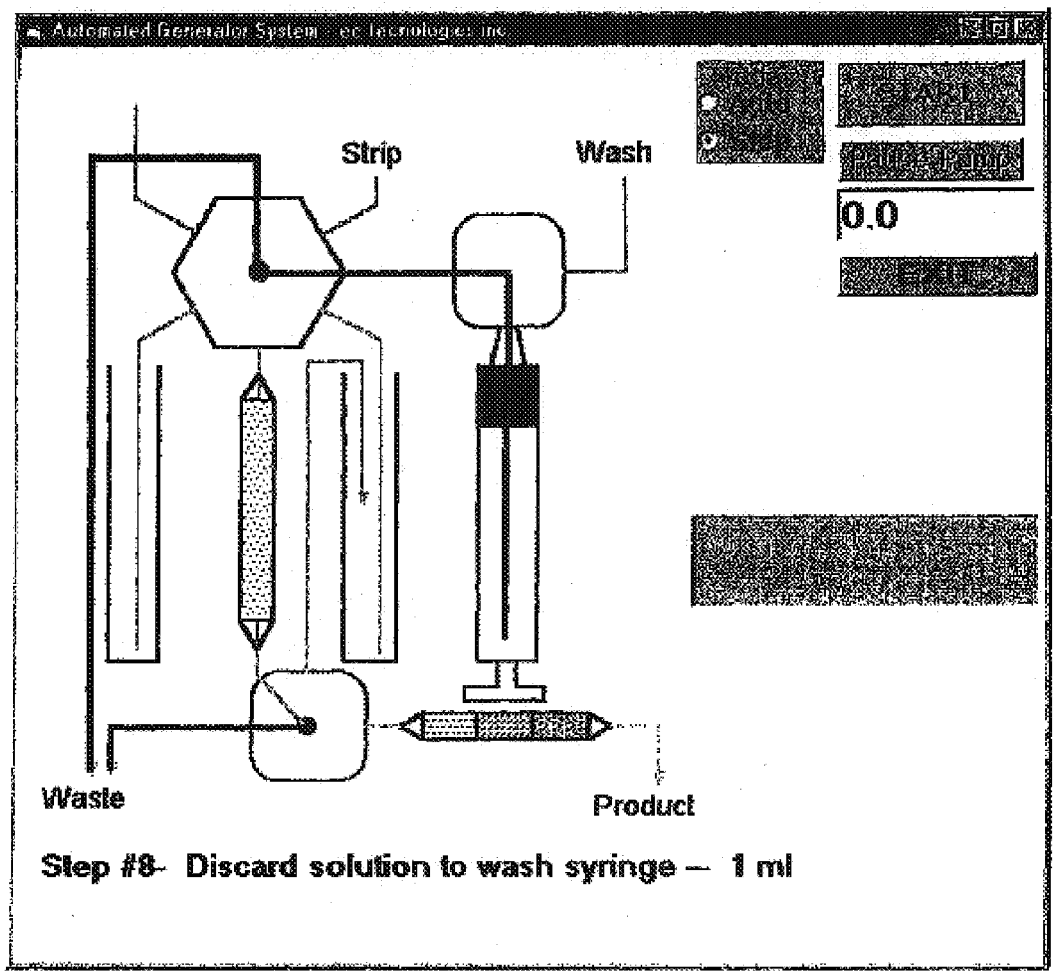
Figure 15:
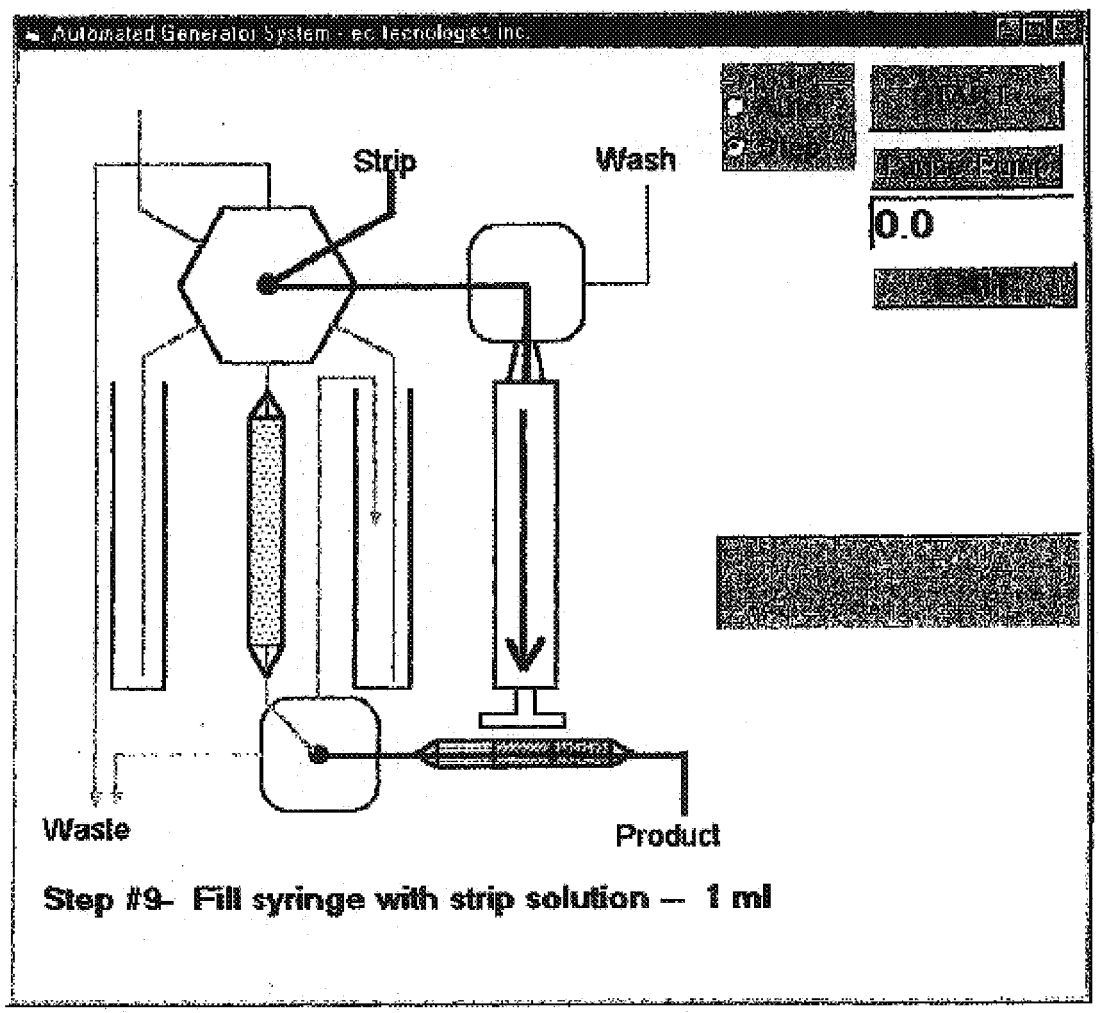
Figure 16:
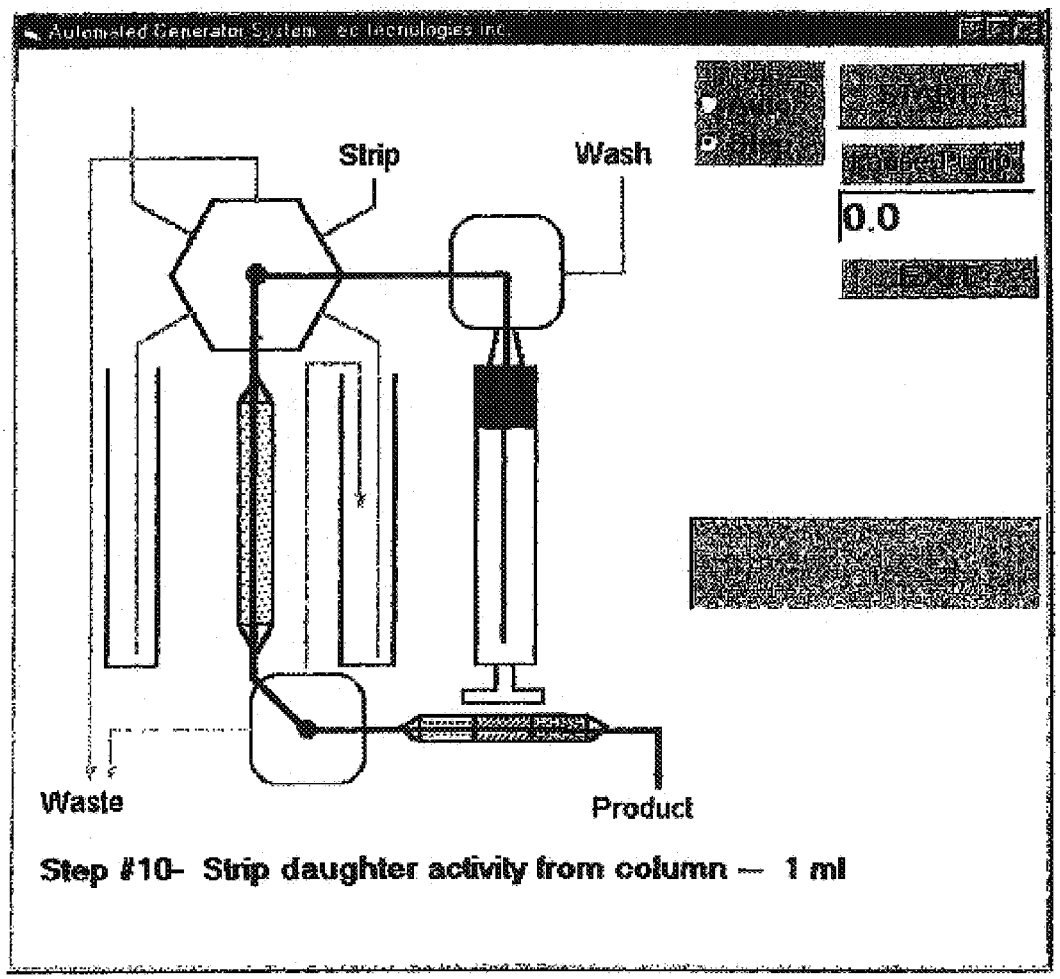
Figure 17:
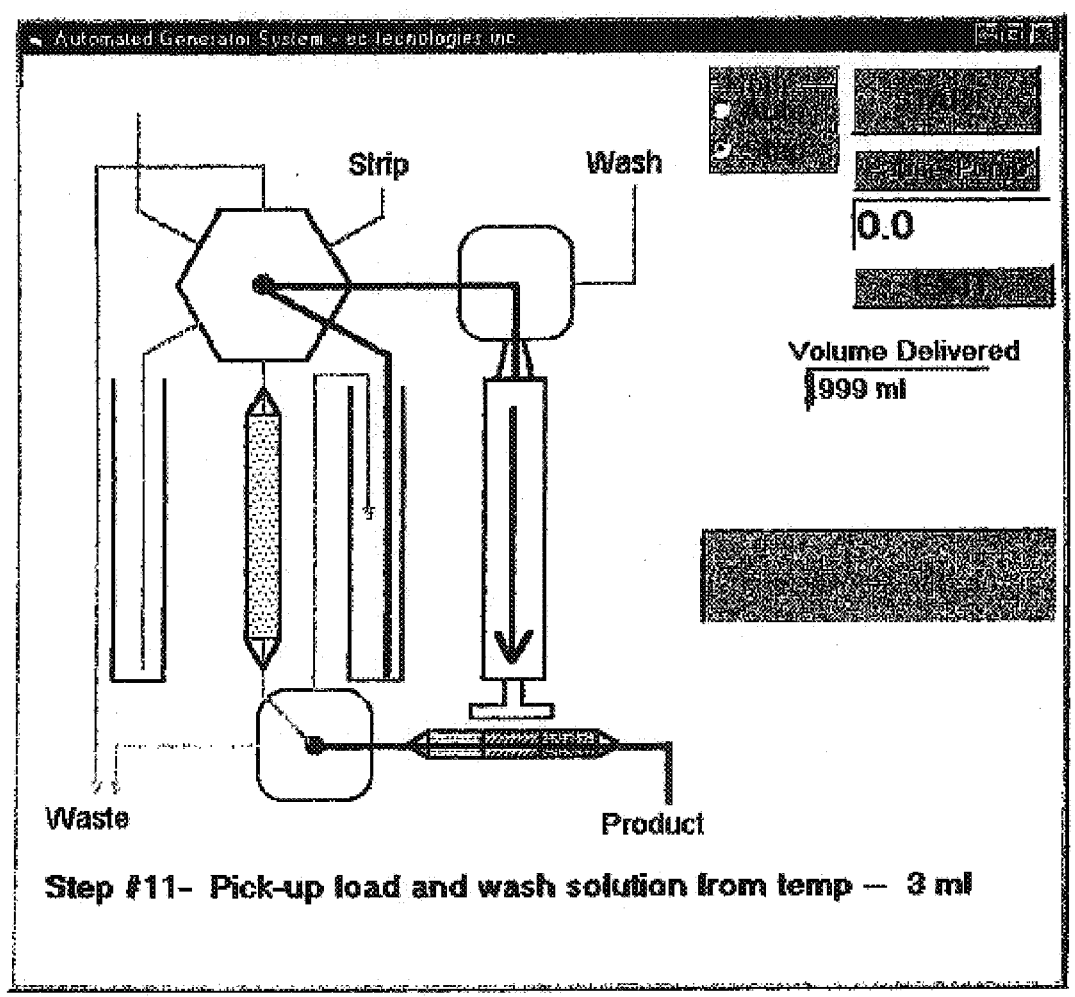

FIG. 13 shows Step #7. In Step #7, a stripping solution is loaded from an external stripping solution container 42. The stripping solution used may be specific to the chromatographic material within the separation column 30 and functions to cause the chromatographic material to release the daughter radionuclide.

In Step #8, the stripping solution is directed to a waste container 48. Drawing in and discarding the initial volume of stripping solution in Step #8 functions to wash the syringe body 18 of any remaining parent radionuclides.

In Steps #9 and 10, the stripping solution is again drawn in and then passed through the separation column 30 and guard column 32. The guard column 32 functions to remove any remaining parent radionuclide still present in the daughter radionuclide. The result (passing to the product container 46) is a highly purified solution of the daughter radionuclide.

In step #11, the parent radionuclide may be retrieved from the temporary storage container 36 and returned to the storage vessel 38.

While the steps of FIGS. 7–17 are shown as occurring in the manual mode, it is to be understood that they may also occur automatically (i.e., each step commencing immediately after conclusion of the preceding step without human intervention). Where performed automatically, the instantaneous flow diagrams shown in FIGS. 7–17 are updated accordingly. A total volume may be displayed along with a relative position of the plunger within the syringe body 18.

The linear actuator 20 may be operated either open or closed loop. Where controlled in a closed loop fashion, feedback of the plunger position may be used to advance the process from one step to the next. Where performed in an open loop mode, a timer 21 may be used to allow the plunger to advance to a predetermined position before advancing to a following process step.

A specific embodiment of a method and apparatus for separating radionuclides has been described for the purpose of illustrating the manner in which the invention is made and used. It should be understood that the implementation of other variations and modifications of the invention and its various aspects will be apparent to one skilled in the art, and that the invention is not limited by the specific embodiments described herein. Therefore, it is contemplated to cover the present invention and any and all modifications, variations, or equivalents that fall within the true spirit and scope of the basic underlying principles disclosed and claimed herein.

```
Option Explicit
'program flags
  Public StopFlag As Integer 'request made to pause operation
  Public RunFlag As Integer 'run has started
  Public BusyFlag As Boolean 'valve controller is moving '   control of pump and valve positions is determined by a comma delineated text
'   file (protocol) this file is prepared and maintaned by a separate progam,
Script Edit 'Script File variables are  input to code via sequential file read, 1 line at a
time
'the following are the variables in each line
    Public StepNumber As String 'sequential step number, not used for control
    Public SyringePumpIndex As Integer 'which of the three syringe pumps
    Public Mode As String '"1" for withdraw(fill), "2" for rapid discharge  or
"3" for infuse (slow)
    Public Volume As Single 'volume of liquid to be transferred by pump
    Public PumpRate As Single 'rate of liquid flow in ml/min
  'current values of valve position
    Public ValveA As Integer 'position of valve 1 (1 to 6)
    Public ValveB As Integer 'same as valve 1 but rage only (1 to 4)
    Public ValveC As Integer 'pump mounted valve (1 to 4)
    Public Comment As String 'description of step
    'Public NewValveA, NewValveB, NewValveC As Integer 'control characters for pump protocols
    Dim ENQ As String * 1
    Dim EOT As String * 1
    Dim ETX As String * 1
    Dim STX As String * 1
    Dim ACK As String * 1
    Dim NAK As String * 1

Const Initialize = 15
    Const mlPerStep = (4.9449 / 2000) 'result of calibration with water in
ml/2000pulses Public mlPerSecond As Single
    Public Volume_in_Syringe As Single
    Public ULstat As Integer
    Public DataValueOut As Integer
    Public DataValueIn As Integer
    Public Counter As Integer
    Public StatusByte As String
    Public StatusByte2 As String
    Public Response As String
    Public Position As Integer
    Public NumberOfSteps As Integer
    Public lasttime As Single
    Public mSecPerStep As Integer
    Public SyringeHeight As Integer
    Public i As Integer
    Public Position_Of_A As Integer
    Public Position_Of_B As Integer
    Public Position_Of_C As Integer
```

```
    Public SyringeVolume As Single
    Public SyringePump As String
    Public LogFileName As String
    Public NumberOfPumps As Integer
    Public FileNum1 As Integer
    Public FileNum2 As Integer
    Public DummyString As String
    Public InfuseDelay As Integer
    Public PumpPulseRate As Integer
    Public DefaultDirectory As String
    Public BoardNum As Integer Private Sub cmdExit_click()
End Sub Private Sub Form_Load()
    AutoForm.Show
'set communication parameters for syringe pump
    MSComm1.CommPort = 1
    MSComm1.InputLen = 0
    MSComm1.Settings = "9600,E,7,1"
    MSComm1.PortOpen = True
    'control characters
    STX = Chr$(2)
    ETX = Chr$(3)
    EOT = Chr$(4)
    ENQ = Chr$(5)
    ACK = Chr$(6)
    NAK = Chr$(21)
    Volume_in_Syringe = 0
'find current directory
    DefaultDirectory = CurDir + "\"
'initial valve position
    ValveA = 1
    ValveB = 1
    ValveC = 3
    LogFileName = DefaultDirectory + "ARSS_log_file.log"
    FileNum2 = FreeFile
    Open LogFileName For Output As #FileNum2
    Print #FileNum2, "File opened"
    Close #FileNum2
    BoardNum = 1 'initial value of board number - scan for valid board number
'set up computer boards digital i/o software/hardware
    ULstat% = cbDeclareRevision(CURRENTREVNUM)
    ULstat% = cbErrHandling(DONTPRINT, DONTSTOP)
        If ULstat% <> 0 Then Stop
    ULstat% = cbDConfigPort(BoardNum, FIRSTPORTA, DIGITALOUT) 'valve 1 command
        If ULstat% <> 0 Then
            BoardNum = 0
            ULstat% = cbErrHandling(PRINTALL, DONTSTOP)
            ULstat% = cbDConfigPort(BoardNum, FIRSTPORTA, DIGITALOUT) 'valve 1 command
                If ULstat% <> 0 Then Stop
        End If
    ULstat% = cbErrHandling(PRINTALL, DONTSTOP)
    ULstat% = cbDConfigPort(BoardNum, FIRSTPORTB, DIGITALOUT) 'valve 2 response
        If ULstat% <> 0 Then Stop
```

```
    ULstat% = cbDConfigPort(BoardNum, FIRSTPORTCL, DIGITALIN) 'valve 1 command
        If ULstat% <> 0 Then Stop
    ULstat% = cbDConfigPort(BoardNum, FIRSTPORTCH, DIGITALIN) 'valve 2 response
        If ULstat% <> 0 Then Stop
    ULstat% = cbDConfigPort(BoardNum, SECONDPORTCL, DIGITALIN) 'valve 1 response
for busy and error
        If ULstat% <> 0 Then Stop
    ULstat% = cbDConfigPort(BoardNum, SECONDPORTCH, DIGITALIN) 'valve 2 response
for busy and error
        If ULstat% <> 0 Then Stop
    SyringeHeight = Shape1.Height
    Shape1.Height = 0
    InitializePump ("01") ' initialize necessary after a reset command
    InitializePump ("02") ' initialize necessary after a reset command
    InitializePump ("03") ' initialize necessary after a reset command
    mnuProtocol.Enabled = True
'check where are valves and show position of them
    Call CheckValvePosition
    Call SetValvePosition("A", Position_Of_A)
    Call SetValvePosition("B", Position_Of_B)
End Sub Private Sub lblValveA_Click(Index As Integer)
    If mnuManual.Checked = True Then Call SetValvePosition("A", Index)
End Sub Private Sub lblValveB_Click(Index As Integer)
    If mnuManual.Checked = True Then Call SetValvePosition("B", Index)
End Sub Private Sub lblValveC_Click(Index As Integer)
    If mnuManual.Checked = True Then Call SetValvePosition("C", Index)
End Sub Private Sub ManDischarge_Click()
    Mode = 1
    Picture2.Picture = LoadPicture(DefaultDirectory + "fast discharge.jpg")
    Call mnuStart_Click
End Sub Private Sub ManFill_Click()
    Mode = 0
    Picture2.Picture = LoadPicture(DefaultDirectory + "fast fill.jpg")
Call mnuStart_Click
End Sub Private Sub ManRate_LostFocus()
Dim Junk As Single
If IsNumeric(ManRate.Text) Then
    Junk = Val(ManRate.Text)
        If Junk < 300# And Junk > 0 Then PumpRate = Junk
End If
    ManRate.Text = Str(PumpRate)
End Sub Private Sub ManVolume_lostfocus()
Dim Junk As Single
```

```
If IsNumeric(ManVolume.Text) Then
    Junk = Val(ManVolume.Text)
        If Junk <= 5# And Junk > 0 Then SyringeVolume = Junk
End If
    ManVolume.Text = Str(SyringeVolume)
End Sub Private Sub mnuManual_Click()
If mnuManual.Checked = True Then
 ManualFrame.Visible = False
 mnuManual.Checked = False
 Else
 ManualFrame.Visible = True
 mnuManual.Checked = True
 mnuStart.Enabled = False
 End If
    End Sub Private Sub PausePump_Click() 'operator stopped run
    If StopFlag Then
        StopFlag = False
        PausePump.Caption = "PAUSE"
        tmrPumpRate.Enabled = True
    Else
        StopFlag = True
        PausePump.Caption = "RESUME"
        tmrPumpRate.Enabled = False
    End If
  End Sub 'manual pump command transmitter - for diagnostic use
Private Sub CommandPump_GotFocus()
    CommandPump.SelStart = 0
    CommandPump.SelLength = Len(CommandPump.Text)
End Sub Private Sub CommandPump_KeyPress(KeyAscii As Integer)
    If KeyAscii = 13 Then Call CommandPump_LostFocus
End Sub Private Sub CommandPump_LostFocus()
    CreateCommandString (CommandPump.Text)
End Sub Private Sub ValveConfigure() ' read script, one line per cycle, set volume, and
valve positions
Dim NewPumpRate As Single
Dim NewValveA, NewValveB, NewValveC As Integer
  If EOF(FileNum1) Then 'protocol is completed
        Comments.Caption = "END OF RUN"
        WriteToLog ("END OF PROTOCOL")
        mnuStart.Enabled = False
        RunFlag = False
        Close #FileNum1 'close out current protocol
        lasttime = 0 'reset timer
        GoTo EndOfChange
        End
```

```
      End If

Beep
  'read next line of protocol text
  Input #FileNum1, StepNumber, SyringePumpIndex, Mode, SyringeVolume,
NewPumpRate, NewValveC, NewValveA, NewValveB, Comment
        If NewValveA > 0 Then ValveA = NewValveA
        If NewValveB > 0 Then ValveB = NewValveB
        If NewValveC > 0 Then ValveC = NewValveC
        If NewPumpRate > 0 Then PumpRate = NewPumpRate
      ManVolume.Text = Str(SyringeVolume)
      ManRate.Text = Str(PumpRate)
    Comments.Caption = "Step #" & StepNumber & "- " & Comment & " -- " &
Str(SyringeVolume) & " ml"
WriteToLog ("STEP #" & StepNumber & " Pump #" & Str(SyringePumpIndex) & " Mode
=" & Mode & " Volume =" & Str(SyringeVolume) & " Rate =" & Str(PumpRate) & "
C=" & Str(NewValveC) & " A =" & Str(NewValveA) & " B =" & Str(NewValveB) &
Comment)
Select Case SyringePumpIndex
      Case Is = 1
          SyringePump = "01"  'required form - ASCII with leading zero for pump
syntax
      Case Is = 2
          SyringePump = "02"
      Case Is = 3
          SyringePump = "03"
      End Select
    MSComm1.Output = EOT + SyringePump + ENQ 'direct all pump requests to new
pump
      WaitASecond (0.1)
      WriteToLog ("SWITCH to pump " & SyringePump)
Select Case Mode ' draw arrow to show fill or dispense
      Case Is = "0"
          Picture2.Picture = LoadPicture(DefaultDirectory + "fast fill.jpg")
      Case Is = "1"
          Picture2.Picture = LoadPicture(DefaultDirectory + "fast discharge.jpg")
End Select
'set up valve positions for next cycle
'Call CheckValvePosition
      If NewValveA = 0 Then GoTo SetValveB
      BusySignA.Visible = True
      Call SetValvePosition("A", NewValveA)

SetValveB:
  'set up valve #2 position for next cycle
    If NewValveB = 0 Then GoTo CheckValves
      BusySignB.Visible = True
      Call SetValvePosition("B", NewValveB)

CheckValves:
'check if valves A & B moved properly
      Call CheckValveBusy 'time to move to position
      Call CheckValvePosition
      If Position_Of_A <> ValveA Then
          WriteToLog ("ERROR Valve A is at " & Str(Position_Of_A) & "should be at "
& Str(ValveA))
          i = MsgBox("Valve A not in Position")
```

```
    End If
    If Position_Of_B <> ValveB Then
        WriteToLog ("ERROR Valve B is at " & Str(Position_Of_B) & "should be at "
& Str(ValveB))
        i = MsgBox("Valve B not in Position")
    End If If NewValveC = 0 Then GoTo EndOfChange
        Call SetValvePosition("C", NewValveC)
EndOfChange:
End Sub
Private Sub CheckValveBusy()
    WaitASecond (0.3) 'need slight delay to let valves start to move before busy
check!!!!
    DataValueIn = 0

Do 'check if A is rotating
        ULstat% = cbDIn(BoardNum, SECONDPORTCL, DataValueIn) ' busy check
        DoEvents
        BusyFlag = DataValueIn And 2 '2nd bit is busy flag
    Loop Until BusyFlag = False
    BusySignA.Visible = False
    If DataValueIn And 1 Then WriteToLog ("Error occured in command to Valve A")
'err bit Do 'busy check B
        ULstat% = cbDIn(BoardNum, SECONDPORTCH, DataValueIn)
        DoEvents
        BusyFlag = DataValueIn And 2 '2nd bit is busy flag
    Loop Until BusyFlag = False
    BusySignB.Visible = False
    If DataValueIn And 1 Then WriteToLog ("Error occured in command to Valve B")

End Sub

Private Sub CheckValvePosition()
    ULstat% = cbDIn(BoardNum, FIRSTPORTCL, Position_Of_A) 'check position A
        If ULstat% <> 0 Then Stop
    ULstat% = cbDIn(BoardNum, FIRSTPORTCH, Position_Of_B) 'check position B
        If ULstat% <> 0 Then Stop
End Sub
Private Sub SetValvePosition(ByVal Valve As String, ByVal Position As Integer)
Dim Rotation As Integer
    Call CheckValvePosition 'where are the valves now
    DataValueOut = Position
    If Valve = "A" Then
    If Position = Position_Of_A Then Exit Sub
    WriteToLog ("VALVE MOVE, Current A =" & Str(Position_Of_A) & ", new =" &
Str(Position))
        Select Case Position_Of_A 'determine shortest rotation path from current
position
            Case Is = 1
                If Position = 2 Or Position = 3 Then DataValueOut = DataValueOut
+ 16 'set clockwise bit
            Case Is = 2
                If Position = 3 Or Position = 4 Then DataValueOut =
DataValueOut + 16
```

```
            Case Is = 3
                If Position = 4 Or Position = 5 Then DataValueOut = DataValueOut
+ 16
            Case Is = 4
                If Position = 5 Or Position = 6 Then DataValueOut =
DataValueOut + 16
            Case Is = 5
                If Position = 6 Or Position = 1 Then DataValueOut = DataValueOut
+ 16
            Case Is = 6
                If Position = 1 Or Position = 2 Then DataValueOut = DataValueOut
+ 16
        End Select
            ULstat% = cbDOut(BoardNum, FIRSTPORTA, DataValueOut)   'move to
position
 'display valve #1 position on screen
   For i = 1 To 6 'clear out all lines used to show flowpattern
        LineA(i).Visible = False 'clear prior lines
        lblValveA(i).ForeColor = &H0&
   Next
        LineA(Position).Visible = True 'display current path
        lblValveA(Position).ForeColor = &HFF&

ElseIf Valve = "B" Then
    If Position = Position_Of_B Then Exit Sub
    WriteToLog ("VALVE MOVE, Current B =" & Str(Position_Of_B) & ", new =" &
Str(Position))
        Select Case Position_Of_B
            Case Is = 1
                If Position = 2 Then DataValueOut = DataValueOut + 16
            Case Is = 2
                If Position = 3 Then DataValueOut = DataValueOut + 16
            Case Is = 3
                If Position = 4 Then DataValueOut = DataValueOut + 16
            Case Is = 4
                If Position = 1 Then DataValueOut = DataValueOut + 16
        End Select
            ULstat% = cbDOut(BoardNum, FIRSTPORTB, DataValueOut)   'move to
position
   For i = 1 To 4 'clear out prior path
        LineB(i).Visible = False
        lblValveB(i).ForeColor = &H0&
   Next
    LineB(Position).Visible = True
    lblValveB(Position).ForeColor = &HFF&

ElseIf Valve = "C" Then
    If Position = Position_Of_C Then Exit Sub ' C's current position not
ascertainable, must be tracked
    WriteToLog ("VALVE MOVE, New C=" & Str(Position))

Rotation = Position * 90 '90 degrees / position
     If Position = 4 Then
            CreateCommandString ("Vv0w" + Trim(Str(Rotation)) + "G")   'clockwise
        Else
            CreateCommandString ("Vv1w" + Trim(Str(Rotation)) + "G")
'counterclocwise
```

```
      End If
    PumpStatus
  'display valve c position on screen
    For i = 1 To 5 'clear out all lines used to show flow pattern
          linec(i).Visible = False
          ' lblvalvec(i).ForeColor = &H0&
    Next
  linec(Position).Visible = True
  linec(Position + 1).Visible = True
  'lblvalvec(Position).ForeColor = &HFF&
  Position_Of_C = Position 'set C's current position
   End If
                If ULstat% <> 0 Then Stop
  End Sub Private Function CalculateBCC(strCommand As String) As String
       Dim strCommandString As String
       Dim i As Integer
       Dim bBCCount As Byte
       Dim bByteValue As Byte strCommandString = strCommand + ETX 'add control character to string
       For i = 1 To Len(strCommandString)
           bByteValue = Asc(Mid(strCommandString, i, 1))
           bBCCount = (bBCCount Xor bByteValue)
        Next i
        CalculateBCC = Chr$(127 - bBCCount) 'invert byte count
  End Function Sub CreateCommandString(strMsg As String)
       Dim strControllerCommand As String
       Dim strCommand As String
       Dim strBCC As String
       Dim i As Integer
       Dim Reply As Integer
           strControllerCommand = strMsg
           strBCC = CalculateBCC(strControllerCommand)
           strCommand = STX + strControllerCommand + ETX + strBCC 'assemble output
  string
             WriteToLog ("COMMAND  " & strCommand)
           Response = "" 'clear input buffer
  TryAgain:
           MSComm1.Output = strCommand  'output command
           WaitASecond (0.1)
           Response = MSComm1.Input 'get reply
           If Left$(Response, 1) = NAK Then
                 ' WriteToLog ("NAK - communication failure, command not acknowledged")
                Reply = MsgBox("NAK", vbRetryCancel, "Communication Failure")
                   If Reply = 4 Then GoTo TryAgain
           End If
               WriteToLog ("       Response =" + Response)
       If Mid$(Response, 3, 1) = "Q" Then
           MSComm1.Output = ACK
           WaitASecond (0.3)
       End If
  End Sub
```

```
Sub WaitASecond(X As Single)
    Dim StartTime As Single
    StartTime = Timer
        Do Until (Timer - StartTime) > X
            DoEvents
        Loop
    End Sub Sub WriteToLog(Message As String)
    FileNum2 = FreeFile
    Open LogFileName For Append As #FileNum2
     Print #FileNum2, Message
     Close #FileNum2
End Sub Sub InitializePump(PumpNumber As String)
    'CreateCommandString ("R")
    'Call SetValvePosition("A", 1)
    'Call CheckValveBusy 'wait for valve to rotate
    MSComm1.Output = EOT + PumpNumber + ENQ
    WaitASecond (0.1)
    MSComm1.Output = STX + "Q" + ETX + "-"
    WaitASecond (0.1)
    CreateCommandString (PumpNumber + "IG")
    If Response <> "" Then NumberOfPumps = NumberOfPumps + 1
    PumpStatus 'wait for pump to init
    CreateCommandString ("Dd130G")
    PumpStatus 'wait for pump to finish
    Call SetValvePosition("C", 4)
End Sub Sub PumpStatus() 'check pump status for motion, cycle until done
Dim Msg As String
Dim Reply As String
TopOfSub:
    CreateCommandString ("Q")
        If Response = "" Then Exit Sub
            StatusByte = Asc(Mid$(Response, 4, 1))
            StatusByte = StatusByte And 31 'eliminate unused bits
        If (StatusByte And 6) Then GoTo TopOfSub ' 2 indicates pump movement, 4
is valve moving
        If (StatusByte And 16) Then '16 is error bit
            CreateCommandString ("E") 'request errors
        If Response = "" Then Exit Sub
            StatusByte = Asc(Mid$(Response, 4, 1)) 'pump error byte
            StatusByte2 = Asc(Mid$(Response, 5, 1)) 'valve error byte
            StatusByte = StatusByte And 15 'eliminate unused bits
            StatusByte2 = StatusByte2 And 15 'eliminate unused bits
        If StatusByte = "0" Then Exit Sub
            Msg = " ERROR Pump -" & Str(StatusByte) & "  Valve ERROR" &
Str(StatusByte2)
            WriteToLog (Msg)
            Reply = MsgBox(Msg, 0, "Error in pump communications")
        End If
End Sub Private Sub mnuAuto_Click()
```

```
    mnuAuto.Checked = True
    mnuStep.Checked = False
    mnuStart.Caption = "Start"
End Sub Private Sub mnuExit_Click()
    If MSComm1.PortOpen = True Then MSComm1.PortOpen = False
    Close #FileNum1
    End
End Sub Private Sub mnuStart_Click()
    mnuStart.Enabled = False
Nextstep:
  NumberOfSteps = SyringeVolume / mlPerStep
    If PumpRate > 0.75 Then 'use pump rate in pulses/sec to control flow rate
        PumpPulseRate = PumpRate / 60 / mlPerStep
        DeliveredVolume.Visible = False
        Label1.Visible = False
    Else 'single step, use time delay to control flow rate
        If Mode = "0" Then CreateCommandString ("Pp1s100G") 'fill syringe slowly
        If Mode = "1" Then CreateCommandString ("Dd1t100G") 'discharge syringe
slowly
        tmrPumpRate.Interval = 1000 / (PumpRate / 60 / mlPerStep) '1 pulse /
interval
        tmrPumpRate.Interval = tmrPumpRate.Interval - 100 ' approximate delay in
processing
        Counter = 0
        tmrPumpRate.Enabled = True 'turn on timer
        DeliveredVolume.Visible = True
        Label1.Visible = True
        PausePump.Visible = True
        Exit Sub
    End If If Mode = "0" Then 'fill syringe with solution
        CreateCommandString ("Pp" + Trim(Str(NumberOfSteps)) + "s" +
Trim(Str(PumpPulseRate) + "G"))
        Call DisplayVolume(PumpRate)
        PumpStatus 'wait for completion
        Volume_in_Syringe = Volume_in_Syringe + SyringeVolume
        Shape1.Height = SyringeHeight * (Volume_in_Syringe / 5)
        If mnuManual.Checked Then Exit Sub
        ValveConfigure
            If mnuAuto.Checked = True And RunFlag = True Then GoTo Nextstep ElseIf Mode = "1" Then 'discharge syringe contents
        CreateCommandString ("Dd" + Trim(Str(NumberOfSteps)) + "t" +
Trim(Str(PumpPulseRate) + "G"))
        Call DisplayVolume(-PumpRate)
        PumpStatus
        Volume_in_Syringe = Volume_in_Syringe - SyringeVolume
        If Volume_in_Syringe < 0 Then Volume_in_Syringe = 0
        Shape1.Height = SyringeHeight * (Volume_in_Syringe / 5)
        If mnuManual.Checked Then Exit Sub
        ValveConfigure
            If mnuAuto.Checked = True And RunFlag = True Then GoTo Nextstep
```

```
    End If
        If RunFlag = True Then mnuStart.Enabled = True 'falls through to this step
if in step mode
End Sub Private Sub mnuStep_Click()
    mnuAuto.Checked = False
    mnuStep.Checked = True
    mnuStart.Caption = "Step"
End Sub Private Sub mnuProtocol_Click()
Dim SyringeRate As Single
'read script file and set up initial conditions
    CommonDialog1.FILTER = "Protocol Scripts | *.PRO"
    CommonDialog1.ShowOpen
    If CommonDialog1.FileName = "" Then Exit Sub
    FileNum1 = FreeFile
    Open CommonDialog1.FileName For Input As FileNum1
    WriteToLog ("PROTOCOL " & CommonDialog1.FileName)
    RunFlag = True
For i = 1 To 6
    Input #FileNum1, DummyString
        lblValveA(i) = DummyString
Next i For i = 1 To 4
    Input #FileNum1, DummyString
        lblValveB(i) = DummyString
Next i For i = 1 To 3
    Input #FileNum1, DummyString
        lblvalvec(i) = DummyString
Next i
    Input #FileNum1, DummyString
    lblCommonA.Caption = DummyString
    Input #FileNum1, DummyString
    lblCommonB.Caption = DummyString ValveConfigure 'read initial valve configuration
    mnuStart.Enabled = True
    mnuMode.Enabled = True
    End Sub Private Sub DisplayVolume(MlperMin)
Dim StartTime As Single
Dim Volume As Single
StartTime = Timer
TopOfSub:
CreateCommandString ("Q")
        If Response = "" Then Exit Sub
        Volume = MlperMin / 60 * (Timer - StartTime)
        If (Volume_in_Syringe + Volume) < 0 Then Exit Sub
        Shape1.Height = SyringeHeight * ((Volume_in_Syringe + Volume) / 5)
            StatusByte = Asc(Mid$(Response, 4, 1))
            StatusByte = StatusByte And 31 'eliminate unused bits
```

```
        If (StatusByte And 2) Then GoTo TopOfSub ' 2 indicates pump movement End Sub
'a timer is necessary to drive pump slow enough, if not utilized, the slowest is
1.5 ml/min
'the timer interval is set in calling code as is number of steps
Sub tmrPumpRate_Timer()
    If Counter > NumberOfSteps Then
    PausePump.Visible = False
    tmrPumpRate.Enabled = False
      If mnuManual.Checked Then Exit Sub
      ValveConfigure
      If mnuAuto.Checked = True And RunFlag = True Then Call mnuStart_Click
      If mnuStep.Checked = True Then mnuStart.Enabled = True
      Exit Sub
    End If
'set up next cycle
    CreateCommandString ("G") 'start pump, parameters already set and are
retained
    If Mode = 0 Then Volume_in_Syringe = Volume_in_Syringe + mlPerStep
    If Mode = 1 Then Volume_in_Syringe = Volume_in_Syringe - mlPerStep
    If Volume_in_Syringe < 0 Then Volume_in_Syringe = 0
    DeliveredVolume.Text = Format((Counter * mlPerStep), ".000 ml")
    Shape1.Height = SyringeHeight * (Volume_in_Syringe / 5) 'update graphic
display
    Counter = Counter + 1
End Sub
```

10178003.062102

```
Option Explicit
    Public RowIndex As Long
    Public ColIndex As Long
    Public Steps As Integer
    Public NewFileFlag As Integer
    Public ProtocolFileName As String
    Public ConfigurationFileName As String
    Public ChangeFlag As Integer
    Dim DataString(200, 0 To 9) As String
    Dim MsgReply As Integer
    Dim StepNumber As Integer
    Dim MsgString As String
    Dim DefaultDirectory As String
    Dim I As Integer, J As Integer Private Sub mnuAddStep_Click()
    Steps = Steps + 1
    grid1.AddItem (Steps)
    DataString(Steps - 1, 0) = Steps
    grid1.Col = 1: grid1.Row = Steps - 1
    Call grid1_click
 End Sub Private Sub mnuConfigurationFile_Click()
Dim I As Integer
Dim x As String
    CfgCommonDialog.ShowOpen
    ConfigurationFileName = (CfgCommonDialog.FileName)
    If ConfigurationFileName = "" Then Exit Sub
        Open ConfigurationFileName For Input As #1
LstA.Clear
LstA.AddItem " "  'No change
For I = 1 To 6
    Input #1, x
    lblValveA(I).Caption = x
    LstA.AddItem x
Next I
LstB.Clear
LstB.AddItem " "  'no change
For I = 1 To 4
    Input #1, x
    lblValveB(I).Caption = x
    LstB.AddItem x
Next I
LstC.Clear
LstC.AddItem " "  'no change
For I = 1 To 3
    Input #1, x
    lblValveC(I).Caption = x
    'LstC.AddItem x
Next I
LstC.AddItem lblValveC(1).Caption + " to " + lblValveC(2).Caption
LstC.AddItem lblValveC(2).Caption + " to " + lblValveC(3).Caption
LstC.AddItem lblValveC(3).Caption + " to Syringe"
LstC.AddItem "Syringe to " + lblValveC(1).Caption
'get labels for common ports on distribution valves
```

```
Input #1, x
CommonA.Caption = x
Input #1, x
CommonB.Caption = x
Close #1
mnuNew.Enabled = True End Sub Private Sub mnuInsertStep_Click()
    StepNumber = grid1.Row + 1
    Steps = Steps + 1
    grid1.AddItem Steps 'add next line
    For I = Steps - 1 To StepNumber Step -1 'move data down from step chosen
        For J = 0 To grid1.Cols - 1
            grid1.TextMatrix(I, J) = grid1.TextMatrix(I - 1, J) 'move data up 1
row
            DataString(I, J) = DataString(I - 1, J)
            grid1.TextMatrix(I - 1, J) = "" 'clear chosen step
            DataString(I - 1, J) = ""
        Next J
    Next I
    For I = 1 To Steps 'renumber steps
        grid1.TextMatrix(I - 1, 0) = I
        DataString(I - 1, 0) = I
    Next I
        ChangeFlag = True
        grid1.Col = 0: grid1.Row = StepNumber - 1
        Call grid1_click
End Sub Private Sub LstA_Click() '6 port Hamilton distribution valve
    If RowIndex = 0 And LstA.ListIndex = 0 Then
        MsgReply = MsgBox("There must be a valid position in the initial row of
the protocol")
        Exit Sub
    End If
    grid1.TextMatrix(RowIndex, ColIndex) = LstA.Text
    DataString(RowIndex, ColIndex) = Str$(LstA.ListIndex)
    Call DisplayPath(RowIndex, ColIndex)
        LstA.Visible = False
        LabelA.Visible = False
        ChangeFlag = True
End Sub Private Sub LstB_Click() '4 port Hamilton distribution valve
    If RowIndex = 0 And LstB.ListIndex = 0 Then
        MsgReply = MsgBox("There must be a valid position in the initial row of
the protocol")
        Exit Sub
    End If
        grid1.TextMatrix(RowIndex, ColIndex) = LstB.Text
            DataString(RowIndex, ColIndex) = Str$(LstB.ListIndex)
            Call DisplayPath(RowIndex, ColIndex)

LstB.Visible = False
        LabelB.Visible = False
```

```
        ChangeFlag = True
End Sub

Private Sub LstC_Click()  '4 port L valve
    If RowIndex = 0 And LstC.ListIndex = 0 Then
        MsgReply = MsgBox("There must be a valid position in the initial row of
the protocol")
        Exit Sub
    End If
        grid1.TextMatrix(RowIndex, ColIndex) = LstC.Text
        DataString(RowIndex, ColIndex) = Str$(LstC.ListIndex)
        Call DisplayPath(RowIndex, ColIndex)
        LstC.Visible = False
        LabelC.Visible = False
        ChangeFlag = True
End Sub Private Sub LstMode_Click()
    grid1.TextMatrix(RowIndex, ColIndex) = LstMode.Text
    DataString(RowIndex, ColIndex) = Str$(LstMode.ListIndex)
    Call DisplayPath(RowIndex, ColIndex)
        LstMode.Visible = False
        ChangeFlag = True
End Sub Private Sub LstSyringe_Click()
        If RowIndex = 0 And LstSyringe.ListIndex = 0 Then
        MsgReply = MsgBox("There must be a valid position in the initial row of
the protocol")
        Exit Sub
    End If
grid1.TextMatrix(RowIndex, ColIndex) = LstSyringe.Text
    DataString(RowIndex, ColIndex) = Str$(LstSyringe.ListIndex)
    'Call DisplayPath(RowIndex, ColIndex)
        LstSyringe.Visible = False
        ChangeFlag = True
End Sub Private Sub mnuConfiguration_Click()
    MainForm.Show
End Sub Private Sub mnuExisting_Click()
Dim FileWord
Dim I As Integer
Dim J As Integer
Dim FileNum1 As Integer
Dim x As String
If ChangeFlag Then I = MsgBox("SAVE Changes??", 4, "Changes made to Protocol")
If I = 6 Then Call mnuSave_Click
If Steps > 0 Then
        For I = 0 To Steps - 2
            grid1.RemoveItem (0)
        Next I
    End If
    ProCommonDialog.ShowOpen
```

```
    ProtocolFileName = (ProCommonDialog.FileName)
    If ProtocolFileName = "" Then Exit Sub
        mnuSave.Enabled = True
        FileNum1 = FreeFile
        Open ProtocolFileName For Input As FileNum1

LstA.Clear
'input labels for valve A
LstA.AddItem " " 'No change
For I = 1 To 6
    Input #FileNum1, x
    lblValveA(I).Caption = x
    LstA.AddItem x
Next I
'labels for valve B
LstB.Clear
LstB.AddItem " " 'No change
For I = 1 To 4
    Input #FileNum1, x
    lblValveB(I).Caption = x
    LstB.AddItem x
Next I
'Valve C
LstC.Clear
LstC.AddItem " " 'no change
For I = 1 To 3
    Input #FileNum1, x
    lblValveC(I).Caption = x
    'LstC.AddItem x
Next I
LstC.AddItem lblValveC(1).Caption + " to " + lblValveC(2).Caption
LstC.AddItem lblValveC(2).Caption + " to " + lblValveC(3).Caption
LstC.AddItem lblValveC(3).Caption + " to Syringe"
LstC.AddItem "Syringe to " + lblValveC(1).Caption
'misc labels and flow rates
    Input #FileNum1, x
        CommonA.Caption = x
    Input #FileNum1, x
        CommonB.Caption = x grid1.Visible = True
    mnuEdit.Enabled = True
    Steps = 0
    Do While Not EOF(1)
            For J = 0 To grid1.Cols - 1
                Input #1, FileWord
                Select Case J
                    Case Is = 0, 3, 4, 8
                        grid1.TextMatrix(Steps, J) = FileWord
                    Case Is = 1
                        grid1.TextMatrix(Steps, J) =
LstSyringe.List(FileWord)
                    Case Is = 2
                        grid1.TextMatrix(Steps, J) = LstMode.List(FileWord)
                    Case Is = 5
                        grid1.TextMatrix(Steps, J) = LstC.List(FileWord)
```

```
                        Case Is = 6
                            grid1.TextMatrix(Steps, J) = LstA.List(FileWord)
                        Case Is = 7
                            grid1.TextMatrix(Steps, J) = LstB.List(FileWord)
                    End Select
                            DataString(Steps, J) = FileWord
                    Next J
                Steps = Steps + 1
                If Not EOF(1) Then grid1.AddItem ""
            Loop
        Close #1
script.Caption = ProtocolFileName
NewFileFlag = False
Text1.Text = ""
grid1.Col = 0
Call grid1_click
EndOfSub:
End Sub Private Sub mnuExit_Click()
Dim I As Integer
    If ChangeFlag Then I = MsgBox("SAVE Changes??", 4, "Changes made to Protocol
or New File Created")
    If I = 6 Then Call mnuSave_Click
    End
End Sub Private Sub mnuNew_Click()
Dim I As Integer
Dim J As Integer
If ChangeFlag Then I = MsgBox("SAVE Changes??", 4, "Changes made to Protocol")
If I = 6 Then Call mnuSave_Click
grid1.Visible = True
NewFileFlag = True
    If Steps > 0 Then
        For I = 0 To Steps - 2
            grid1.RemoveItem (0)
        Next I For J = 0 To grid1.Cols - 1
            grid1.TextMatrix(0, J) = ""
            DataString(0, J) = ""
        Next J
    End If
    mnuSave.Enabled = True
'following are default positions of valves when unit is first turn on
DataString(0, 0) = "1"
DataString(0, 1) = "1"
DataString(0, 2) = "0"
DataString(0, 3) = "1.0"
DataString(0, 4) = "10.0"
DataString(0, 5) = "3"
DataString(0, 6) = "1"
DataString(0, 7) = "1"
grid1.TextMatrix(0, 0) = "1"
```

```
    grid1.TextMatrix(0, 1) = LstSyringe.List(1)
    grid1.TextMatrix(0, 2) = LstMode.List(0)
    grid1.TextMatrix(0, 3) = "1.0"
    grid1.TextMatrix(0, 4) = "10.0"
    grid1.TextMatrix(0, 5) = LstC.List(3)
    grid1.TextMatrix(0, 6) = LstA.List(1)
    grid1.TextMatrix(0, 7) = LstB.List(1)
    grid1.TextMatrix(0, 8) = "Default Valve Positions"
    ProtocolFileName = ""
    Steps = 1
    ChangeFlag = False
    grid1.Col = 0
    Call grid1_click End Sub Private Sub mnuSave_Click()
    Dim I As Integer
    Dim J As Integer
    Dim FileNum1 As Integer
    On Error GoTo EndOfSub
    ProCommonDialog.ShowSave
    ProtocolFileName = (ProCommonDialog.FileName)
    FileNum1 = FreeFile
    Open ProtocolFileName For Output As FileNum1
'output labels for valve A
    For I = 1 To 6
        Print #FileNum1, lblValveA(I).Caption
    Next I
'labels for valve B
    For I = 1 To 4
        Print #FileNum1, lblValveB(I).Caption
    Next I
'Valve C
    For I = 1 To 3
        Print #FileNum1, lblValveC(I).Caption
    Next I
'misc labels and flow rates
    Print #FileNum1, CommonA.Caption
    Print #FileNum1, CommonB.Caption For I = 0 To Steps - 1
        For J = 0 To grid1.Cols - 2
            Print #FileNum1, DataString(I, J) & ", ";
        Next J
        Print #FileNum1, Chr(34); DataString(I, J); Chr(34)
    Next I
    Close #FileNum1
    ChangeFlag = False
EndOfSub:
End Sub Private Sub MnuDeleteStep_Click()
    StepNumber = grid1.Row + 1
    MsgString = "Do you want to remove step " + Str$(StepNumber)
    MsgReply = MsgBox(MsgString, vbOKCancel, "REMOVE STEP FROM SCRIPT")
    If MsgReply = 2 Then Exit Sub
```

```
        grid1.RemoveItem (grid1.Row) 'remove from grid
        For I = StepNumber To Steps
                For J = 0 To 6
                    DataString(I - 1, J) = DataString(I, J) 'remove from storage
arrray
            Next J
        Next I
        Steps = Steps - 1
        For I = 1 To Steps 'renumber steps
            grid1.TextMatrix(I - 1, 0) = I
            DataString(I - 1, 0) = I
        Next I
End Sub Private Sub Form_Load() 'set width of each field in grid
Dim I As Integer
Dim x As String
        grid1.ColWidth(0) = 400  'Step
        grid1.ColWidth(1) = 600  'Syringe 1-3
        grid1.ColWidth(2) = 1200 'Mode
        grid1.ColWidth(3) = 600  'Volume
        grid1.ColWidth(4) = 600  'Pumping rate
        grid1.ColWidth(5) = 1500 'Valve 1 "C  part of ALH syringe "
        grid1.ColWidth(6) = 1500 'Valve 2 "A"
        grid1.ColWidth(7) = 1500 'valve 3 "B"
        grid1.ColWidth(8) = 3950 'Description Steps = 0
LstSyringe.AddItem "   "  'no change
LstSyringe.AddItem "01"
LstSyringe.AddItem "02"
LstSyringe.AddItem "03"

LstMode.AddItem "Fill"
LstMode.AddItem "Discharge"
DefaultDirectory = CurDir + "\"
Label1.Caption = "Step   Syringe     Mode              ml        ml/min
Syringe Valve        Valve A              Valve B
Description of Step"
Label2.Caption = "                                              Volume
Rate"
End Sub Private Sub grid1_click()
    RowIndex = grid1.Row
    ColIndex = grid1.Col
    If ColIndex = 0 Then
        Call DisplayPath(RowIndex, 2)
        Call DisplayPath(RowIndex, 5)
        Call DisplayPath(RowIndex, 6)
        Call DisplayPath(RowIndex, 7)
    End If
    LstA.Visible = False
    LstB.Visible = False
    LstC.Visible = False
    LstMode.Visible = False
```

```
        LstSyringe.Visible = False

LabelA.Visible = False
    LabelB.Visible = False
    LabelC.Visible = False

Select Case ColIndex
        Case Is = 0
            Exit Sub
        Case Is = 1
            LstSyringe.Visible = True
            LstSyringe.Width = grid1.CellWidth
            LstSyringe.Top = grid1.CellTop + grid1.Top
            LstSyringe.Left = grid1.CellLeft + grid1.Left
        Case Is = 2 'set pump operation mode
            LstMode.Visible = True
            LstMode.Width = grid1.CellWidth
            LstMode.Top = grid1.CellTop + grid1.Top
            LstMode.Left = grid1.CellLeft + grid1.Left
        Case Is = 5
            LstC.Visible = True
            LstC.Width = grid1.CellWidth
            LstC.Top = grid1.CellTop + grid1.Top
            LstC.Left = grid1.CellLeft + grid1.Left
            LabelC.Visible = True
        Case Is = 6
            LstA.Visible = True
            LstA.Width = grid1.CellWidth
            LstA.Top = grid1.CellTop + grid1.Top
            LstA.Left = grid1.CellLeft + grid1.Left
            LabelA.Visible = True
        Case Is = 7
            LstB.Visible = True
            LstB.Width = grid1.CellWidth
            LstB.Top = grid1.CellTop + grid1.Top
            LstB.Left = grid1.CellLeft + grid1.Left
            LabelB.Visible = True
        Case Else
            Text1.Visible = True
            Text1.Text = grid1.Text
            Text1.Width = grid1.CellWidth
            Text1.Top = grid1.CellTop + grid1.Top
            Text1.Left = grid1.CellLeft + grid1.Left
            Text1.SetFocus
    End Select
End Sub Private Sub Text1_GotFocus()
    Text1.SelStart = 0
    Text1.SelLength = Len(Text1.Text)
End Sub Private Sub Text1_KeyPress(KeyAscii As Integer)
        ChangeFlag = True
    If KeyAscii = 13 Then
        Call CheckEntry
```

```
                If grid1.Col = grid1.Cols - 1 And NewFileFlag Then Call
mnuAddStep_Click: Exit Sub
                If grid1.Col < grid1.Cols - 1 Then grid1.Col = grid1.Col + 1
'move focus right 1 column
        Call grid1_click
     End If
End Sub Private Sub Text1_LostFocus()
    Call CheckEntry
End Sub Private Sub DisplayPath(ByVal Step, Column)
Dim I As Integer
topofsub:
Select Case Column 'which valve or pump to display
    Case Is = 2      'MODE OF PUMP OPERATION Select Case Val(DataString(Step, Column))
             Case Is = 0
                   SyringePicture.Picture = LoadPicture(DefaultDirectory +
"fast fill.jpg")
             Case Is = 1
                   SyringePicture.Picture =
LoadPicture("DefaultDirectory+fast discharge.jpg")
            End Select
    Case Is = 5 '      DIRECTION OF VALVE C  integral with pump
        For I = 1 To 5
            linec(I).Visible = False
        '    lblValveC(I).ForeColor = &H0&
        Next I I = Val(DataString(Step, Column))
               If I = 0 Then 'no change requested so draw path from line/s
above
                   Step = Step - 1
                   If Step >= 0 Then GoTo topofsub
               Else
                   linec(I).Visible = True
                   linec(I + 1).Visible = True
         '  lblValveC(I).ForeColor = &HFF&
               End If Case Is = 6   'DIRECTION OF VALVE A
            For I = 1 To 6
               LineA(I).Visible = False
               lblValveA(I).ForeColor = &H0&
                  Next I
             I = Val(DataString(Step, Column))
                If I = 0 Then 'no change requested so draw path from line/s
above
                    Step = Step - 1
                    If Step >= 0 Then GoTo topofsub
                Else
                    LineA(I).Visible = True
                    lblValveA(I).ForeColor = &HFF&
                End If
```

```
    Case Is = 7 '        DIRECTION OF VALVE B
        For I = 1 To 4
            LineB(I).Visible = False
            lblValveB(I).ForeColor = &H0&
        Next I
            I = Val(DataString(Step, Column))
            If I = 0 Then 'no change requested so draw path from line/s above
               Step = Step - 1
               If Step >= 0 Then GoTo topofsub
            Else
               LineB(I).Visible = True
               lblValveB(I).ForeColor = &HFF&
            End If
            End Select
End Sub
Private Sub CheckEntry()
Dim TestWord As Single
Select Case ColIndex
    Case Is = 3 'volume of liquid to be pumped
        If IsNumeric(Text1.Text) Then
            TestWord = Val(Text1.Text)
            If TestWord > 0 And TestWord <= 5 Then
                grid1.TextMatrix(RowIndex, ColIndex) = Text1.Text
                DataString(RowIndex, ColIndex) = Text1.Text
            End If
        End If
    Case Is = 4 'rate to be pumped
        If IsNumeric(Text1.Text) Then
            TestWord = Val(Text1.Text)
            If TestWord > 0.05 And TestWord <= 300 Then
                grid1.TextMatrix(RowIndex, ColIndex) = Text1.Text
                DataString(RowIndex, ColIndex) = Text1.Text
            End If
        End If
    Case Is = 8
                grid1.TextMatrix(RowIndex, ColIndex) = Text1.Text
                DataString(RowIndex, ColIndex) = Text1.Text
End Select
    Text1.Visible = False
End Sub
```

What is claimed is:

1. An apparatus for automatically separating radionuclides using a chromatographic separation process, such apparatus comprising:

means for forming a first flow diagram depicting flow of the radionuclides through a first set of separation elements of the plurality of separation processing elements, but only during a first step of the chromatographic separation process;

means for displaying a first flow diagram depicting flow of the radionuclides through a first set of separation elements of the plurality of separation processing elements, but only during a first step of the chromatographic separation process;

means for forming a second flow diagram depicting flow of the radionuclides through a second set of separation elements of the plurality of separation processing elements, but only during a second step of the chromatographic separation process; and means for displaying a second flow diagram depicting flow of the radionuclides through a second set of separation elements of the plurality of separation processing elements, but only during a second step of the chromatographic separation process, said means for displaying a first flow diagram and said means for displaying a second flow diagram allowing an operator to monitor the separation processing elements without directly viewing the separation processing elements.

2. The apparatus for automatically separating radionuclides as in claim 1 wherein a separation processing element of the plurality of separation processing elements further comprises a separation column containing a chromatographic material.

3. The apparatus for automatically separating radionuclides as in claim 2 further comprising means for withdrawing a parent radionuclide from a shipping container.

4. The apparatus for automatically separating radionuclides as in claim 3 further comprising means for transferring the parent radionuclide to a second container wherein radioactive decay produces a desired daughter radionuclide.

5. The apparatus for automatically separating radionuclides as in claim 4 further comprising means for loading the separation column with the daughter and parent radionuclides.

6. The apparatus for automatically separating radionuclides as in claim 5 wherein the means for loading the separation column with the daughter and parent radionuclides further comprises means for passing the parent and daughter radionuclides through the separation column, thereby allowing capture of one of the parent and daughter radionuclides by the separation column.

7. The apparatus for automatically separating radionuclides as in claim 6 wherein the means for passing the daughter and parent radionuclides through the separation column further comprises means for routing the radionuclides that have passed through the separation column to a storage container.

8. The apparatus for automatically separating radionuclides as in claim 7 further comprising means for withdrawing the parent radionuclide from the storage container.

9. The apparatus for automatically separating radionuclides as in claim 8 further comprising means for returning the parent radionuclide to the growth container for regrowth of daughter radionuclides.

10. The apparatus for automatically separating radionuclides as in claim 9 further comprising means for equilibrating the separation column with the solution to be passed through the separation column.

11. The apparatus for automatically separating radionuclides as in claim 6 further comprising means for withdrawing a wash solution from a vessel containing wash solution.

12. The apparatus for automatically separating radionuclides as in claim 11 further comprising means for flushing the separation column with the wash solution to remove any residual parent radionuclides.

13. The apparatus for automatically separating radionuclides as in claim 12 further comprising means for withdrawing a strip solution from a vessel containing strip solution.

14. The apparatus for automatically separating radionuclides as in claim 13 further comprising means for stripping the daughter radionuclide from the separation column by passing the stripping solution through the separation column.

15. The apparatus for automatically separating radionuclides as in claim 14 further comprising means for capturing any remaining traces of the parent radionuclide from the daughter radionuclide using a second column containing one or more chromatographic materials serving as a guard column.

16. An apparatus for automatically separating radionuclides using a chromatographic separation process having at least two steps, such apparatus comprising:

a processor for forming an active display flow of the radionuclides through a plurality of separation processing elements during the chromatographic separation process;

a controller adapted to control flow of the radionuclides through the plurality of separation processing elements during each step of the chromatographic separation process; and a display operatively coupled to the controller and adapted to actively display flow of the radionuclides through the plurality of separation processing elements during the chromatographic separation process.

17. The apparatus for automatically separating radionuclides as in claim 16 wherein a separation processing element of the plurality of separation processing elements further comprises a separation column containing a chromatographic material.

18. The apparatus for automatically separating radionuclides as in claim 17 further comprising a syringe pump adapted to withdraw a parent radionuclide from a shipping container.

19. The apparatus for automatically separating radionuclides as in claim 18 further comprising a first valve arrangement adapted to transfer the parent radionuclide to a second container wherein radioactive decay produces a desired daughter radionuclide.

20. The apparatus for automatically separating radionuclides as in claim 19 further comprising a second valve arrangement adapted to pass the parent and daughter radio nuclides through the separation column, thereby allowing capture of the daughter radionuclides by the separation column and discharge of the parent radionuclides into a storage container.

21. The apparatus for automatically separating radionuclides as in claim 20 further comprising a third valve arrangement adapted to flush the separation column with the wash solution to remove any residual parent radionuclides.

22. The apparatus for automatically separating radionuclides as in claim 21 further comprising a fourth valve arrangement adapted to strip the daughter radionuclide from the separation column by passing the stripping solution through the separation column.

23. The apparatus for automatically separating radionuclides as in claim 22 further comprising a guard column adapted to capture any remaining traces of the parent radionuclide remaining within the stripped daughter radionuclide.

* * * * *